(12) United States Patent
Stelfox et al.

(10) Patent No.: US 10,218,399 B2
(45) Date of Patent: Feb. 26, 2019

(54) SYSTEMS AND METHODS FOR ACTIVITY DETERMINATION BASED ON HUMAN FRAME

(71) Applicant: Zebra Technologies Corporation, Lincolnshire, IL (US)

(72) Inventors: Jill Stelfox, San Jose, CA (US); Michael A. Wohl, Rogersville, TN (US); James J. O'Hagan, Lincolnshire, IL (US); Cynthia Traeger, Fairfax, VA (US)

(73) Assignee: Zebra Technologies Corporation, Lincolnshire, IL (US)

(*) Notice: Subject to any disclaimer, the term of this patent is extended or adjusted under 35 U.S.C. 154(b) by 0 days.

(21) Appl. No.: 15/349,606

(22) Filed: Nov. 11, 2016

(65) Prior Publication Data

US 2017/0056721 A1 Mar. 2, 2017

Related U.S. Application Data

(63) Continuation of application No. 14/205,216, filed on Mar. 11, 2014, now Pat. No. 9,531,415.
(Continued)

(51) Int. Cl.
*G06K 7/00* (2006.01)
*H04B 1/10* (2006.01)
(Continued)

(52) U.S. Cl.
CPC .......... *H04B 1/1036* (2013.01); *A41D 1/002* (2013.01); *A41D 1/005* (2013.01); *A41D 1/04* (2013.01);
(Continued)

(58) Field of Classification Search
CPC ............... A63B 24/00; A63B 24/0021; A63B 2024/0025; A63B 2220/836;
(Continued)

(56) References Cited

U.S. PATENT DOCUMENTS

| 3,732,500 | A | 5/1973 | Dishal et al. |
| 4,270,145 | A | 6/1981 | Farina |

(Continued)

FOREIGN PATENT DOCUMENTS

| EP | 1235077 A2 | 8/2002 |
| EP | 1241616 A2 | 9/2002 |

(Continued)

OTHER PUBLICATIONS

International Search Report and Written opinion from International Application No. PCT/US2014/040881 dated Nov. 4, 2014.
(Continued)

*Primary Examiner* — Andrew W Bee

(57) ABSTRACT

Systems and related methods providing for determining activities of individuals are discussed herein. Circuitry may be configured to wirelessly receive tag signals from a plurality of RF location tags. Two or more of the RF location tags may be positioned on an individual, such as at positions that may at least partially define a human frame. The circuitry may be configured to correlate the two or more RF location tags with the individual. Location data for each of the two or more RF location tags may be determined based on the received tag signals. An activity of the individual may be determined based on the location data. In some embodiments, one or more activities involving multiple individuals may be determined based on RF location tags and sensors positioned on each of the multiple individuals. Furthermore, sensor data from the sensors may be communicated over the UWB channel.

14 Claims, 8 Drawing Sheets

Related U.S. Application Data

(60) Provisional application No. 61/831,990, filed on Jun. 6, 2013.

(51) Int. Cl.
| | | |
|---|---|---|
| *G06F 17/30* | (2006.01) | |
| *H04L 29/08* | (2006.01) | |
| *A63B 24/00* | (2006.01) | |
| *G06K 7/10* | (2006.01) | |
| *G16H 50/50* | (2018.01) | |
| *G08C 17/02* | (2006.01) | |
| *H04B 1/7097* | (2011.01) | |
| *H04W 4/02* | (2018.01) | |
| *A63B 71/06* | (2006.01) | |
| *G06K 9/00* | (2006.01) | |
| *G06N 5/02* | (2006.01) | |
| *H04L 12/26* | (2006.01) | |
| *G06Q 50/20* | (2012.01) | |
| *G09B 19/00* | (2006.01) | |
| *H04B 1/7163* | (2011.01) | |
| *H04B 1/719* | (2011.01) | |
| *G06Q 50/22* | (2018.01) | |
| *H04Q 9/00* | (2006.01) | |
| *A41D 1/00* | (2018.01) | |
| *A41D 1/04* | (2006.01) | |
| *A42B 3/30* | (2006.01) | |
| *G16H 50/30* | (2018.01) | |
| *G05B 15/02* | (2006.01) | |
| *G06N 7/00* | (2006.01) | |
| *G06F 19/00* | (2018.01) | |
| *G06K 17/00* | (2006.01) | |
| *G06Q 90/00* | (2006.01) | |

(52) U.S. Cl.
CPC ............ *A42B 3/30* (2013.01); *A63B 24/0021* (2013.01); *A63B 24/0062* (2013.01); *A63B 71/06* (2013.01); *A63B 71/0619* (2013.01); *A63B 71/0622* (2013.01); *A63B 71/0686* (2013.01); *G05B 15/02* (2013.01); *G06F 17/3087* (2013.01); *G06F 17/30864* (2013.01); *G06F 17/30876* (2013.01); *G06F 17/30879* (2013.01); *G06F 19/00* (2013.01); *G06K 7/10227* (2013.01); *G06K 7/10297* (2013.01); *G06K 7/10306* (2013.01); *G06K 7/10366* (2013.01); *G06K 9/00342* (2013.01); *G06N 5/02* (2013.01); *G06N 7/005* (2013.01); *G06Q 50/20* (2013.01); *G06Q 50/22* (2013.01); *G08C 17/02* (2013.01); *G09B 19/0038* (2013.01); *G16H 50/30* (2018.01); *G16H 50/50* (2018.01); *H04B 1/7097* (2013.01); *H04B 1/719* (2013.01); *H04B 1/71635* (2013.01); *H04B 1/71637* (2013.01); *H04L 43/04* (2013.01); *H04L 67/12* (2013.01); *H04Q 9/00* (2013.01); *H04W 4/02* (2013.01); *A41D 2600/10* (2013.01); *A63B 24/00* (2013.01); *A63B 2024/0025* (2013.01); *A63B 2024/0028* (2013.01); *A63B 2024/0056* (2013.01); *A63B 2220/12* (2013.01); *A63B 2220/40* (2013.01); *A63B 2220/836* (2013.01); *A63B 2225/50* (2013.01); *A63B 2225/54* (2013.01); *G06K 2017/0045* (2013.01); *G06Q 90/00* (2013.01)

(58) Field of Classification Search
CPC ............ A63B 2225/50; A63B 2225/54; G06K 2017/0045; G06K 7/10306; G06K 7/10297; G06K 9/00342
See application file for complete search history.

(56) References Cited

U.S. PATENT DOCUMENTS

| | | |
|---|---|---|
| 5,046,133 A | 9/1991 | Watanabe et al. |
| 5,119,104 A | 6/1992 | Heller |
| 5,469,409 A | 11/1995 | Anderson et al. |
| 5,513,854 A | 5/1996 | Daver |
| 5,645,077 A | 7/1997 | Foxlin |
| 5,699,244 A | 12/1997 | Clark et al. |
| 5,901,172 A | 5/1999 | Fontana et al. |
| 5,920,287 A | 7/1999 | Belcher et al. |
| 5,930,741 A | 7/1999 | Kramer |
| 5,995,046 A | 11/1999 | Belcher et al. |
| 6,028,626 A | 2/2000 | Aviv |
| 6,121,926 A | 9/2000 | Belcher et al. |
| 6,176,837 B1 | 1/2001 | Foxlin |
| 6,204,813 B1 | 3/2001 | Wadell et al. |
| 6,366,242 B1 | 4/2002 | Boyd et al. |
| 6,380,894 B1 | 4/2002 | Boyd et al. |
| 6,593,885 B2 | 7/2003 | Wisherd et al. |
| 6,655,582 B2 | 10/2003 | Wohl et al. |
| 6,710,713 B1 | 3/2004 | Russo |
| 6,812,884 B2 | 11/2004 | Richley et al. |
| 6,836,744 B1 | 12/2004 | Asphahani et al. |
| 6,882,315 B2 | 4/2005 | Richley et al. |
| 7,009,638 B2 | 3/2006 | Gruber et al. |
| 7,190,271 B2 | 3/2007 | Boyd et al. |
| 7,263,133 B1 | 8/2007 | Miao |
| 7,667,604 B2 | 2/2010 | Ebert et al. |
| 7,671,802 B2 | 3/2010 | Walsh et al. |
| 7,710,322 B1 | 5/2010 | Ameti et al. |
| 7,739,076 B1 | 6/2010 | Vock et al. |
| 7,755,541 B2 | 7/2010 | Wisherd et al. |
| 7,899,006 B2 | 3/2011 | Boyd |
| 7,969,348 B2 | 6/2011 | Baker et al. |
| 8,009,727 B2 | 8/2011 | Hui et al. |
| 8,023,917 B2 | 9/2011 | Popescu |
| 8,077,981 B2 | 12/2011 | Elangovan et al. |
| 8,269,835 B2 | 9/2012 | Grigsby |
| 8,279,051 B2 | 10/2012 | Khan |
| 8,289,185 B2 | 10/2012 | Alonso |
| 8,477,046 B2 | 3/2013 | Alonso |
| 8,457,392 B2 | 6/2013 | Cavallaro et al. |
| 8,568,278 B2 | 10/2013 | Riley et al. |
| 8,665,152 B1 | 3/2014 | Kling et al. |
| 8,696,458 B2 | 4/2014 | Foxlin et al. |
| 8,705,671 B2 | 4/2014 | Ameti et al. |
| 8,775,916 B2 | 7/2014 | Pulsipher et al. |
| 8,795,045 B2 | 8/2014 | Sorrells et al. |
| 8,842,002 B2 | 9/2014 | Rado |
| 8,780,204 B2 | 10/2014 | DeAngelis et al. |
| 8,989,880 B2 | 3/2015 | Wohl et al. |
| 9,081,076 B2 | 7/2015 | Deangelis et al. |
| 9,185,361 B2 | 11/2015 | Curry |
| 9,381,645 B1 | 7/2016 | Yarlagadda et al. |
| 2001/0010541 A1 | 8/2001 | Fernandez et al. |
| 2001/0030625 A1 | 10/2001 | Doles et al. |
| 2002/0004398 A1 | 1/2002 | Ogino et al. |
| 2002/0041284 A1 | 4/2002 | Konishi et al. |
| 2002/0114493 A1 | 8/2002 | McNitt et al. |
| 2002/0116147 A1 | 8/2002 | Vock et al. |
| 2002/0130835 A1 | 9/2002 | Brosnan |
| 2002/0135479 A1 | 9/2002 | Belcher et al. |
| 2003/0090387 A1 | 5/2003 | Lestienne et al. |
| 2003/0095186 A1 | 5/2003 | Aman et al. |
| 2003/0128100 A1 | 7/2003 | Burkhardt et al. |
| 2003/0163287 A1 | 8/2003 | Vock et al. |
| 2003/0227453 A1 | 12/2003 | Beier et al. |
| 2004/0022227 A1 | 2/2004 | Lynch et al. |
| 2004/0062216 A1 | 4/2004 | Nicholls et al. |
| 2004/0108954 A1 | 6/2004 | Richley et al. |
| 2004/0178960 A1 | 9/2004 | Sun |
| 2004/0249969 A1 | 12/2004 | Price |

(56) References Cited

U.S. PATENT DOCUMENTS

| | | |
|---|---|---|
| 2004/0260470 A1 | 12/2004 | Rast |
| 2004/0260828 A1 | 12/2004 | Price |
| 2005/0026563 A1 | 2/2005 | Leeper et al. |
| 2005/0031043 A1 | 2/2005 | Paquelet |
| 2005/0059998 A1 | 3/2005 | Norte et al. |
| 2005/0075079 A1 | 4/2005 | Jei et al. |
| 2005/0093976 A1 | 5/2005 | Valleriano |
| 2005/0148281 A1 | 7/2005 | Sanchez-Castro et al. |
| 2005/0207617 A1 | 9/2005 | Sarnoff |
| 2006/0067324 A1 | 3/2006 | Kim |
| 2006/0139167 A1 | 6/2006 | Davie et al. |
| 2006/0164213 A1 | 7/2006 | Burghard et al. |
| 2006/0252476 A1 | 11/2006 | Bahou |
| 2006/0264730 A1 | 11/2006 | Stivoric et al. |
| 2006/0271912 A1 | 11/2006 | Mickle et al. |
| 2006/0281061 A1 | 12/2006 | Hightower et al. |
| 2007/0091292 A1 | 4/2007 | Cho et al. |
| 2007/0176749 A1 | 8/2007 | Boyd et al. |
| 2007/0296723 A1 | 12/2007 | Williams |
| 2008/0065684 A1 | 4/2008 | Zilberman |
| 2008/0106381 A1 | 5/2008 | Adamec et al. |
| 2008/0113787 A1 | 5/2008 | Alderucci |
| 2008/0129825 A1 | 6/2008 | DeAngelis et al. |
| 2008/0140233 A1 | 6/2008 | Seacat |
| 2008/0186231 A1 | 6/2008 | Aljadeff et al. |
| 2008/0182724 A1 | 7/2008 | Guthrie |
| 2008/0204248 A1 | 8/2008 | Winget et al. |
| 2008/0262885 A1 | 10/2008 | Jain et al. |
| 2008/0266131 A1 | 10/2008 | Richardson et al. |
| 2008/0269016 A1 | 10/2008 | Ungari et al. |
| 2008/0281443 A1 | 11/2008 | Rogers |
| 2008/0285805 A1 | 11/2008 | Luinge et al. |
| 2009/0048044 A1 | 2/2009 | Oleson et al. |
| 2009/0141736 A1 | 6/2009 | Becker |
| 2009/0210078 A1 | 8/2009 | Crowley |
| 2009/0231198 A1* | 9/2009 | Walsh .............. A63B 24/0021 342/463 |
| 2010/0026809 A1 | 2/2010 | Curry |
| 2010/0045508 A1 | 2/2010 | Ekbal et al. |
| 2010/0054304 A1 | 3/2010 | Barnes et al. |
| 2010/0060452 A1 | 3/2010 | Schuster et al. |
| 2010/0117837 A1 | 5/2010 | Stirling et al. |
| 2010/0150117 A1 | 6/2010 | Aweya et al. |
| 2010/0228314 A1 | 9/2010 | Goetz |
| 2010/0250305 A1 | 9/2010 | Lee et al. |
| 2010/0278386 A1 | 11/2010 | Hoeflinger |
| 2010/0283630 A1 | 11/2010 | Alonso |
| 2010/0328073 A1 | 12/2010 | Nikitin et al. |
| 2011/0002223 A1 | 1/2011 | Gross |
| 2011/0025847 A1 | 2/2011 | Park et al. |
| 2011/0054782 A1 | 3/2011 | Kaahui et al. |
| 2011/0063114 A1 | 3/2011 | Ikoyan |
| 2011/0064023 A1 | 3/2011 | Yamamoto et al. |
| 2011/0084806 A1 | 4/2011 | Pekins et al. |
| 2011/0132378 A1* | 6/2011 | Levendowski .......... A61B 5/11 128/848 |
| 2011/0134240 A1 | 6/2011 | Anderson et al. |
| 2011/0140970 A1 | 6/2011 | Fukagawa et al. |
| 2011/0159939 A1 | 6/2011 | Lin et al. |
| 2011/0169959 A1 | 7/2011 | DeAngelis et al. |
| 2011/0188513 A1 | 8/2011 | Christoffersson et al. |
| 2011/0195701 A1 | 8/2011 | Cook et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0065483 A1 | 3/2012 | Chung et al. |
| 2012/0081531 A1 | 4/2012 | DeAngelis et al. |
| 2012/0112904 A1 | 5/2012 | Nagy et al. |
| 2012/0126973 A1 | 5/2012 | DeAngelis et al. |
| 2012/0136231 A1* | 5/2012 | Markel .............. A61B 5/0015 600/388 |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0218301 A1 | 8/2012 | Miller |
| 2012/0225676 A1 | 9/2012 | Boyd et al. |
| 2012/0231739 A1 | 9/2012 | Chen et al. |
| 2012/0246795 A1 | 10/2012 | Scheffler et al. |
| 2012/0256745 A1 | 10/2012 | Plett et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0040574 A1 | 2/2013 | Hillyard |
| 2013/0041590 A1 | 2/2013 | Burich et al. |
| 2013/0066448 A1 | 3/2013 | Alonso |
| 2013/0076645 A1 | 3/2013 | Anantha et al. |
| 2013/0096704 A1 | 4/2013 | Case |
| 2013/0115904 A1 | 5/2013 | Kapoor et al. |
| 2013/0138386 A1 | 5/2013 | Jain et al. |
| 2013/0142384 A1 | 6/2013 | Ofek |
| 2013/0257598 A1 | 10/2013 | Kawaguchi et al. |
| 2013/0289382 A1* | 10/2013 | Rofougaran ........ H04L 12/6418 600/407 |
| 2013/0339156 A1 | 12/2013 | Sanjay et al. |
| 2014/0055588 A1 | 2/2014 | Bangera et al. |
| 2014/0145828 A1 | 5/2014 | Bassan-Eskenazi |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0320660 A1 | 10/2014 | DeAngelis et al. |
| 2014/0361875 A1 | 12/2014 | O'Hagan et al. |
| 2014/0361906 A1 | 12/2014 | Hughes et al. |
| 2014/0364141 A1 | 12/2014 | O'Hagan et al. |
| 2014/0365415 A1 | 12/2014 | Stelfox et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0355311 A1 | 12/2015 | O'Hagan et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0378002 A1 | 12/2015 | Hughes et al. |
| 2015/0379387 A1 | 12/2015 | Richley |
| 2016/0059075 A1 | 3/2016 | Molyneux et al. |
| 2016/0097837 A1 | 4/2016 | Richley et al. |

FOREIGN PATENT DOCUMENTS

| | | |
|---|---|---|
| EP | 1253438 A2 | 10/2002 |
| EP | 1503513 A1 | 2/2005 |
| EP | 2474939 A1 | 11/2012 |
| WO | 1998/005977 A1 | 2/1998 |
| WO | 1999/061936 A1 | 12/1999 |
| WO | 2001/008417 A1 | 2/2001 |
| WO | 2006/022548 A1 | 3/2006 |
| WO | 2010/083943 A1 | 7/2010 |
| WO | 2015/051813 A1 | 4/2014 |
| WO | 2014/197600 A1 | 12/2014 |

OTHER PUBLICATIONS

International Search Report and Written opinion from International Application No. PCT/US2014/040940 dated Dec. 17, 2014.
Complaint before the United States District Court of Massachusetts, Civil Action No. 1:15-cv-12297, Lynx System Developers, Inc. et al. V. Zebra Enterprise Solutions Corporation et al., filed Jun. 10, 2015.
International Search Report and Written Opinion from International Application No. PCT/US2014/041062 dated Oct. 1, 2014.
International Search Report and Written Opinion from International Application No. PCT/US2014/040947 dated Oct. 9, 2014.
Fontana, R.J., Richley, E., Barney, J., "Commercialization of an Ultra Wideband Precision Assest Location System", 2003 IEEE

(56) References Cited

OTHER PUBLICATIONS

Conference on Ultra Wideband Systems and Technologies, Nov. 16-19, 2003.
Guèziec, A., "Tracking Pitches for Broadcast Television," Computer, Mar. 2002, pp. 38-43 <http://www.trianglesoftware.com/pitch_tracking.htm>.
CattleLog Pro, eMerge Interactive, Inc., Sebastian, FL, 2004.
Marchant, J., "Secure Animal Indentification and Source Verification", JM Communications, UK, 2002.
"A guide to Using Nlis Approved Ear Tags and Rumen Boluses", National Livestock Identification Scheme, Meat & Livestock Australia Limited, North Sydney, Australia, May 2003.
King L., "NAIS Cattle ID Pilot Projects Not Needed, Since Proven Advanced Technology Already Exists", ScoringSystem, Inc., Sarasota, FL, Dec. 27, 2005. (www.prweb.com/releases2005/12prweb325888.htm).
"RFID in the Australian Meat and Livestock Industry", Allflex Australia Pty Ltd., Capalaba, QLD (AU), Data Capture Suppliers Guide, 2003-2004.
Swedberg, Claire, "USDA Reseachers Develop System to Track Livestock Feeding Behavior Unobtrusively", RFID Journal, Jul. 18, 2013.
Invitation to Pay Additional Fees/Partial International Search Report for PCT/IB2015/054099 dated Oct. 6, 2015.
Swedberg, C., "N.J. Company Seeks to Market Passive Sensor RFID Tags," RFID Journal, Jun. 14, 2011, pp. 1-2 <http://www.rfidjournal.com/articles/pdf?8527>.
International Search Report and Written Opinion for International Application No. PCT/IB2015/054099 dated Dec. 9, 2015.
U.S. Appl. No. 14/296,703, filed Jun. 5, 2014; In re: Alonso et al., entitled Method and Apparatus for Associating Radio Frequency Identification Tags with Participants.
U.S. Appl. No. 61/895,548, filed Oct. 25, 2013, In re: Alonso et al., entitled "Method, Apparatus, and Computer Program Product for Collecting Sporting Event Data Based on Real Time Data for Proximity and Movement of Objects."
International Search Report and Written Opinion for International Application No. PCT/IB2015/059264 dated Feb. 10, 2016.
Jinyun Zhang et al., "UWB Systems for Wireless Sensor Networks", Proceedings of the IEEE, IEEE. New York, US, vol. 97, No. 2, Feb. 1, 2009 (Feb. 1, 2009), pp. 313-331.
International Search Report and Written Opinion for International Application No. PCT/US2015/034267 dated Sep. 25, 2015.
International Search Report and Written Opinion for International Application No. PCT/IB2015/054103 dated Aug. 14, 2015.
Cheong, P. et al., "Synchronization, TOA and Position Estimation for Low-Complexity LDR UWB Devices", Ultra-Wideband, 2005 IEEE International Conference, Zurich, Switzerland Sep. 5-8, 2005, Piscataway, NJ, USA, IEEE, Sep. 5, 2005, pp. 480-484.
International Search Report and Written Opinion for International Application No. PCT/IB2015/054213 dated Aug. 6, 2015.
Wang, Y. et al., "An Algorithmic and Systematic Approach from Improving Robustness of TOA-Based Localization", 2013 IEEE 10th International Conference on High Performance Computing and Communications & 2013 IEEE, Nov. 2013, pp. 2066-2073.
Guvenc, I. et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.
International Search Report and Written Opinion for International Application PCT/IB2015/054102 dated Nov. 4, 2015.
"Seattleite wins top prize in Microsoft's Super Bowl tech Contest", San Francisco AP, Komonews.com, Feb. 5, 2016. <http://komonews.com/news/local/seattleite-wins-top-prize-in-microsofts-super-bowl-tech-contest>.
Bahle et al., "I See You: How to Improve Wearable Activity Recognition by Leveraging Information from Environmental Cameras," Pervasive Computing and Communications Workshops, IEEE International Conference, (Mar. 18-22, 2013).
Teixeira et al., "Tasking Networked CCTV Cameras and Mobile Phones to Identify and Localize Multiple People," Ubicomp '10 Proceedings of the 12th ACM International Conference on Ubiquitous Computing, pp. 213-222 (Sep. 26-29, 2010).
Complaint before the United States District Court of Massachusetts, Civil Action No. 1:15-cv-12297, Lynx System Developers, Inc. et al. V. Zebra Enterprise Solutions Corporation et al., filed Mar. 23, 2016.
Defendant's Answer to Complaint before the United States District Court of Massachusetts, Civil Action No. 1:15-cv-12297, Lynx System Developers, Inc. et al. V. Zebra Enterprise Solutions Corporation et al., filed Apr. 6, 2016.
International Search Report and Written Opinion for International Application No. PCT/US2014/053647 dated Dec. 19, 2014.
International Search Report and Written Opinion for International Application No. PCT/US2016/035614 dated Sep. 15, 2016.
Zhu et al., "A Real-Time Articulated Human Motion Tracking Using Tri-Axis Inertial/Magnetic Sensors Package," IEEE Transactions on Neural Systems and Rehabilitation Engineering, vol. 12, No. 2, Jun. 2004, pp. 295-302.
European Search Report for European Patent Application No. 14806811.7 dated Dec. 1, 2016.

* cited by examiner

SYSTEMS AND METHODS FOR ACTIVITY DETERMINATION BASED ON HUMAN FRAME

CROSS-REFERENCE TO RELATED APPLICATION

This application claims priority from and is a continuation of U.S. patent application Ser. No. 14/205,216 filed Mar. 11, 2014, now U.S. Pat. No. 9,531,415 which claims priority to and the benefit of the filing date of U.S. Provisional Patent Application No. 61/831,990, filed Jun. 6, 2013, the contents of each are incorporated by reference in their entirety herein.

FIELD

Embodiments of the invention relate, generally, to monitoring individuals using a radio frequency ("RF") system.

BACKGROUND

The movement of individuals (e.g., persons, patients, athletes, animals, machines, etc.) can be leveraged for purposes such as determining their activity and/or the characteristics of their activity. In this regard, areas for improving current systems have been identified.

BRIEF SUMMARY

Through applied effort, ingenuity, and innovation, solutions to improve such systems have been realized and are described herein. In general, techniques are provided to improve determination of activities of individuals and groups of individuals (e.g., players in a football game) as well as characteristics of such activities using a RF system.

Some embodiments may provide for a method for determining activity. The method may include: wirelessly receiving signals from a plurality of radio frequency (RF) location tags, e.g., ultra-wideband (UWB) tags, over a UWB communications channel; correlating two or more RF location tags of the plurality of RF location tags with an individual, wherein the two or more RF location tags are located on the individual; determining tag location data for each of the two or more RF location tags based on the tag signals; and determining an activity of the individual based on the tag location data. For example, receiving the signals from the plurality of RF location tags may include receiving UWB signals from the plurality of RF location tags at one or more UWB receivers.

In some embodiments, the two or more RF location tags may be each located on the individual at locations such that the two or more RF location tags at least partially define a human frame. For example, at least one of the two or more RF location tags is located at or near the individual's head, shoulder, elbow, wrist, knee, or foot.

Some embodiments of the method may further include correlating each of the two or more RF location tags with a position on the individual where the two or more RF location tags are each positioned. For example, the signals may include tag placement data indicating a position on the individual where each of the two or more RF location tags is positioned. Additionally and/or alternatively, the signals from the two or more RF location tags may include individual identifying data indicating an identity of the individual. Correlating the two or more RF location tags of the plurality of RF location tags with the individual may further include correlating the two or more RF location tags with the individual from a plurality of individuals each having associated RF location tags.

In some embodiments, correlating two or more RF location tags of the plurality of RF location tags with the individual may include calculating a determined body distance between at least a first RF location tag and a second RF location tag of the two or more of RF location tags. In one embodiment, RF location tags may be associated with the individual, such as in a preliminary registration step.

In some embodiments, determining the tag location data for each of two or more RF location tags based on the tag signals may include determining an arrival time at one or more receivers for each of the tag signals. Furthermore, determining the activity of the individual based on the tag location data may include determining location over time for at least one of the two or more RF location tags; determining spatial proximity of a first RF location tag of the two or more RF location tags relative to a second RF location tag of the two or more RF location tags; determining spatial proximity of a first RF location tag of the two or more RF location tags relative to a second RF location tag of the two or more RF location tags over time; determining whether the individual is within a predetermined area, determining a characteristic of the activity including one or more of a speed, acceleration, momentum and movement path of at least one of the two or more RF location tags; and/or determining spatial proximity of one or more of the two or more RF location tags with one or more of the plurality of RF location tags positioned on a second individual.

In some embodiments, the method may further include wirelessly receiving sensor data from one or more sensors positioned on the individual via the UWB communications channel and wherein determining the activity of the person is based on the sensor data. For example, at least one of the one or more sensors may be co-located with at least one of the two or more RF location tags. Furthermore, the one or more sensors may each be any of or combinations of an accelerometer, a near field communication (NFC) sensor, a proximity detector, a heat sensor, an eye dilation sensor, a hydration sensor, an environmental sensor, a heart rate sensor, a blood pressure sensor, and a blood chemistry sensor.

In some embodiments, the two or more RF location tags and/or sensors each receive power from a common power supply. In some embodiments, power may be received from at least one of heat and moisture generated by the individual.

In some embodiments, the method may further include wirelessly receiving proximity data from one or more near field communication (NFC) sensors positioned on the individual. Here, determining the activity of the person may be further based on the proximity data. For example, the proximity data may indicate that at least one of the one or more NFC sensors is in close proximity to an individual.

Some embodiments of the method may include determining one or more characteristics of the activity. The characteristics of the activity may be determined by location data, proximity data, or combinations thereof. Furthermore, the method may include providing a graphical display of the one or more characteristics of the activity.

In some embodiments, the method may further include determining a collective activity and/or characteristics of the collective activity of two or more individuals. The collective activity may be based on tag location data and/or sensor data received from RF location tags and/or sensors positioned on each of the two or more individuals.

Still other embodiments are directed to a method of monitoring an individual comprising: wirelessly receiving tag signals from a plurality of RF location tags positioned on the individual; determining tag location data for each of the plurality of RF location tags based on the tag signals; calculating a determined body distance between a pair of tags selected from the plurality of RF location tags based on the tag location data; receiving a reference body distance; and comparing the determined body distance to the reference body distance.

In some embodiments, the method of monitoring an individual further comprises identifying individual profile information for the individual from a database based on the comparing the determined body distance to the reference body distance. The method for monitoring an individual may further comprise determining an activity for the individual based on the comparing the determined body distance to the reference body distance.

In still other embodiments, the method for monitoring an individual may further comprise determining an event based on the comparing the determined body distance to the reference body distance.

In still other embodiments, the method for monitoring an individual may further comprise receiving sensor derived data from one or more sensors positioned on the individual, and identifying individual profile information for the individual from a database based on the comparing the determined body distance to the reference body distance and on the sensor derived data.

In still other embodiments, the method for monitoring an individual may further comprise receiving sensor derived data from one or more sensors positioned on the individual, and determining an activity for the individual based on the comparing the determined body distance to the reference body distance and on the sensor derived data.

In still other embodiments, the method for monitoring an individual may further comprise receiving sensor derived data from one or more sensors positioned on the individual, and determining an event based on the comparing the determined body distance to the reference body distance and on the sensor derived data.

Some embodiments may include an apparatus and/or system configured to implement the methods and/or other functionality discussed herein. In other words, the apparatus may include one or more processors and/or other machine components configured to implement the functionality discussed herein based on instructions and/or other data stored in memory and/or other non-transitory computer readable media.

These characteristics as well as additional features, functions, and details of various embodiments are described below. Similarly, corresponding and additional embodiments are also described below.

BRIEF DESCRIPTION OF THE DRAWINGS

Figure 1:
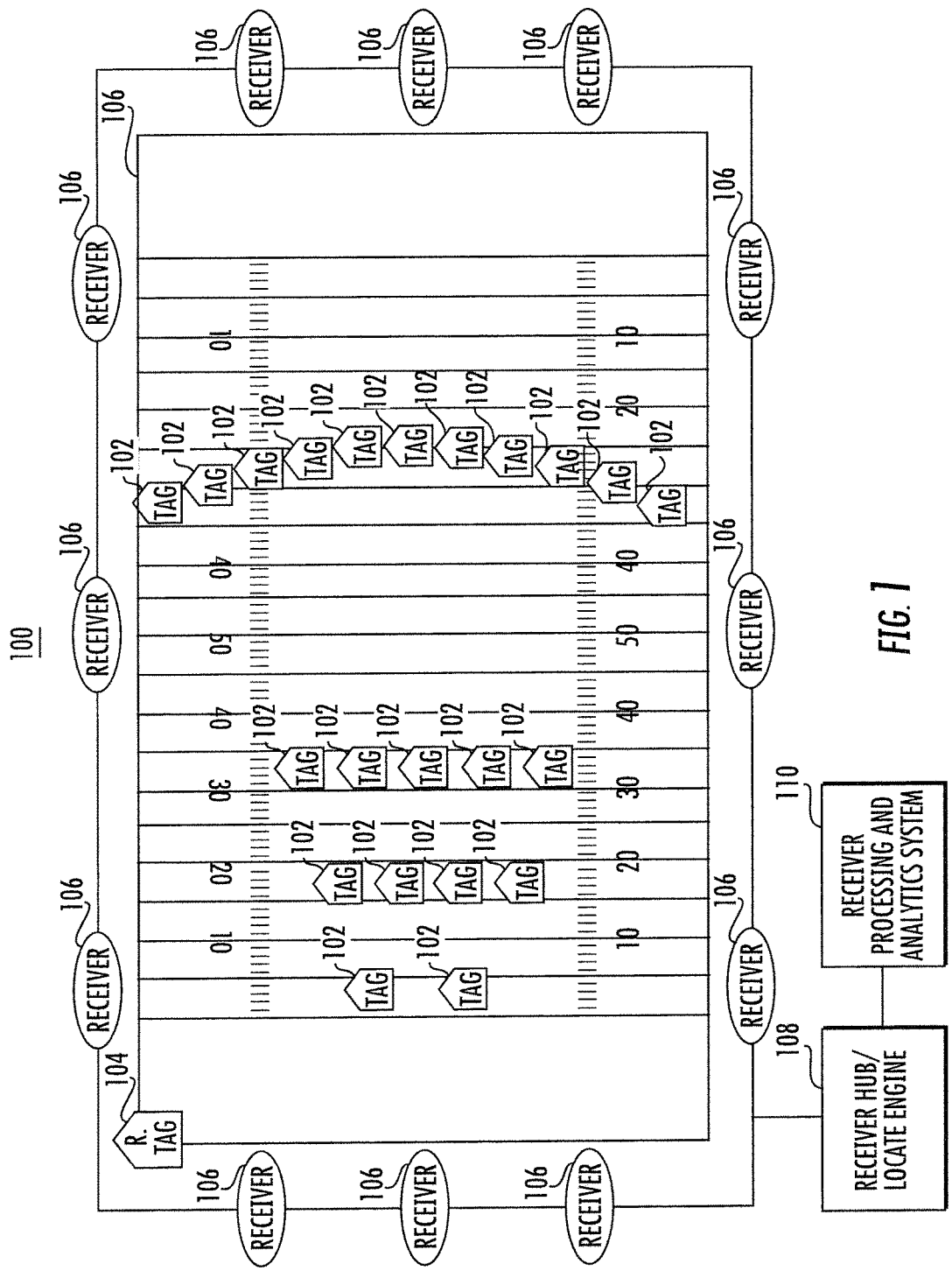
Figure 2:
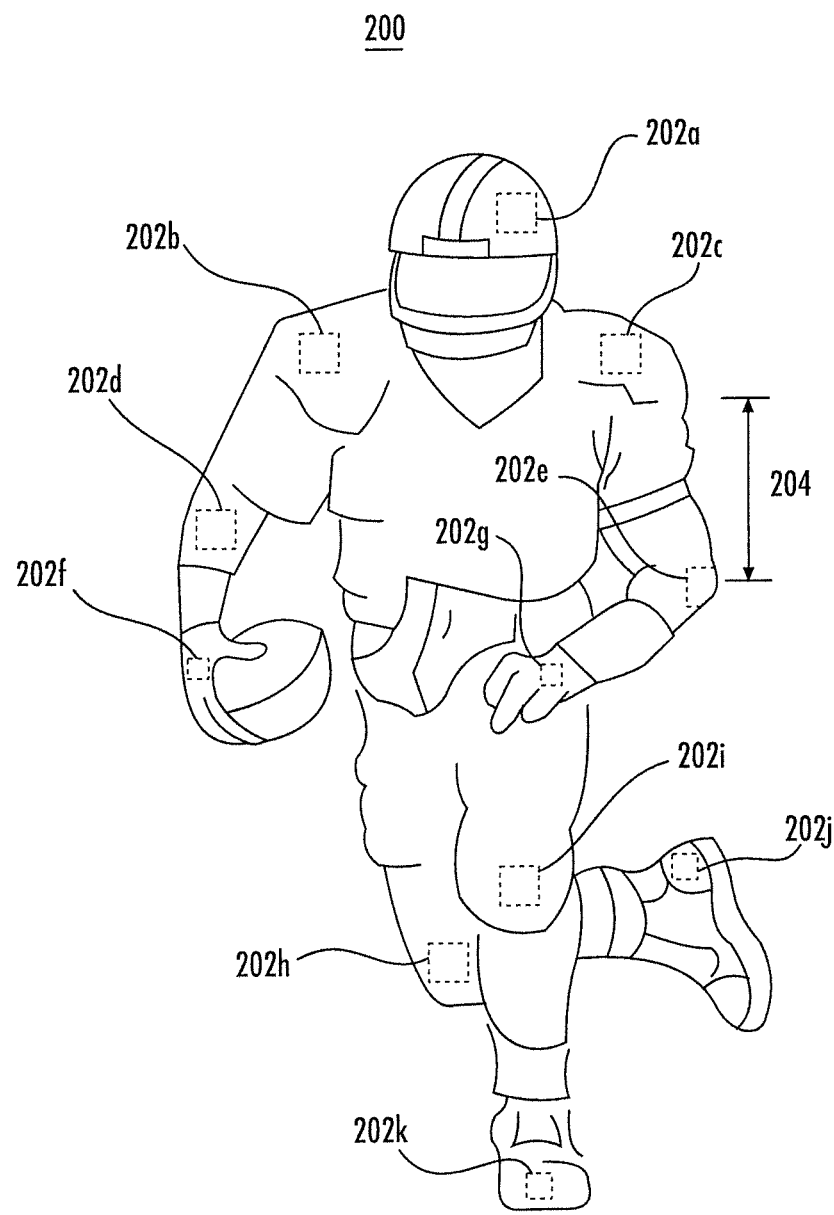
Figure 3:
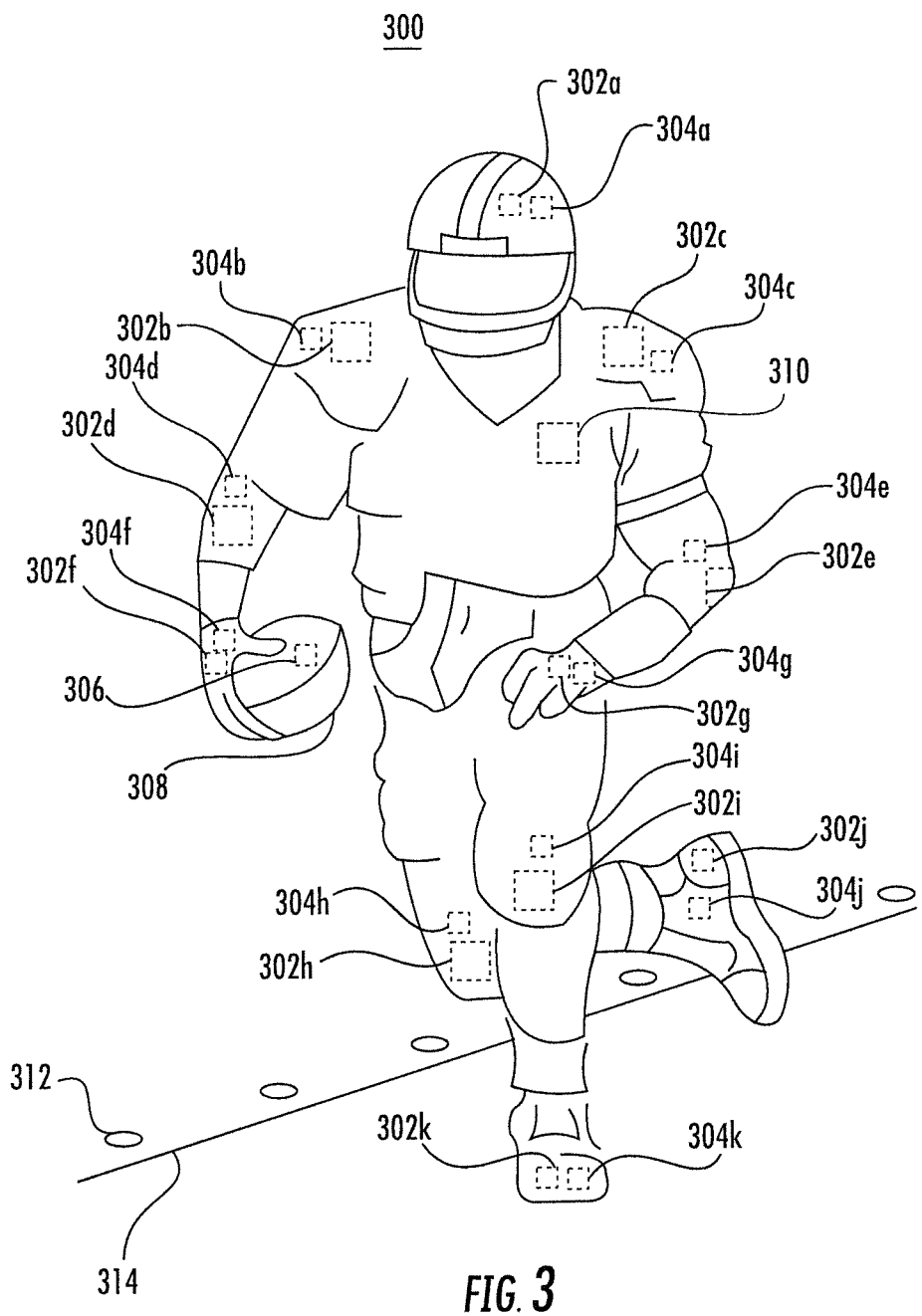
Figure 4A:
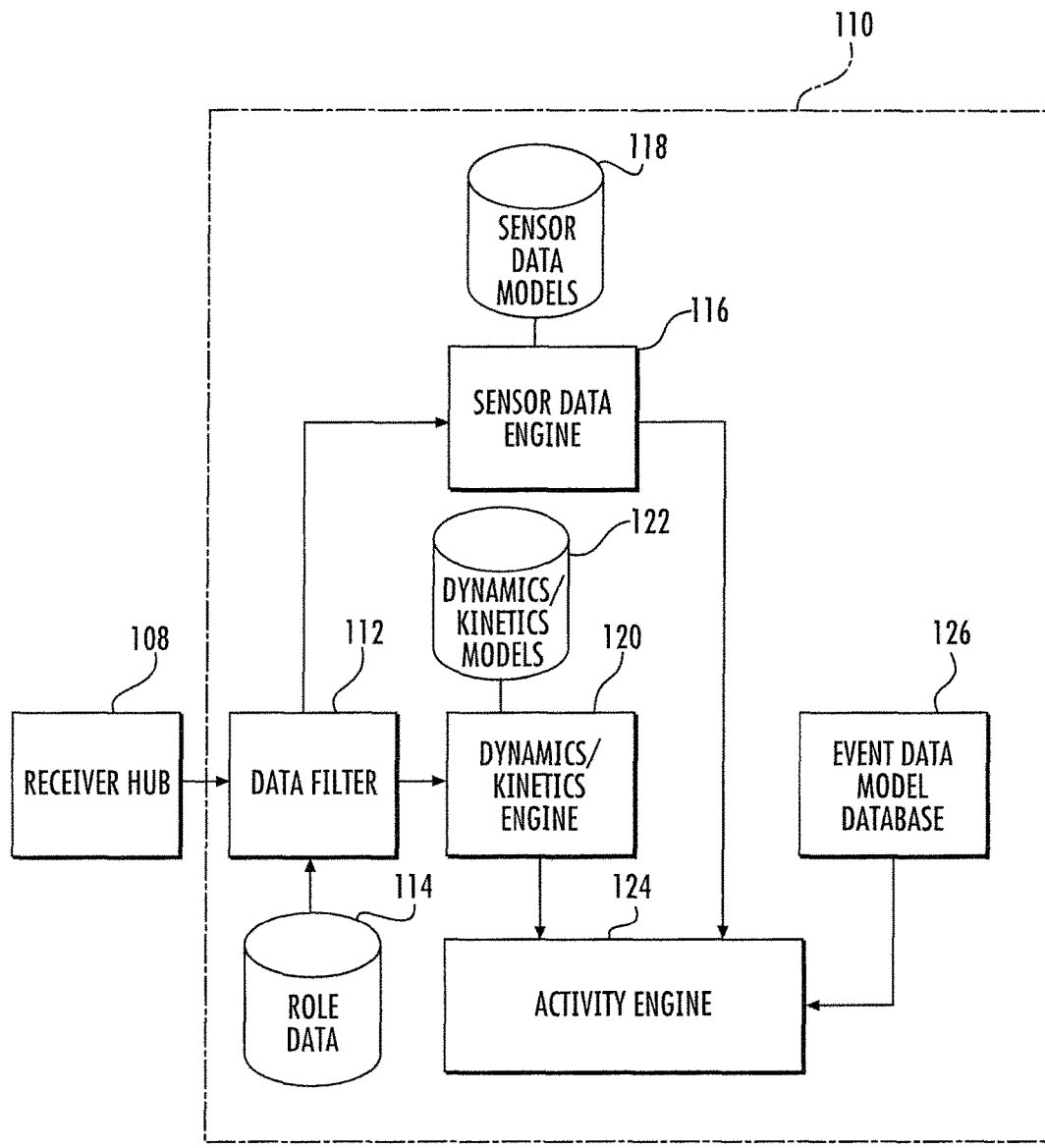
Figure 4B:
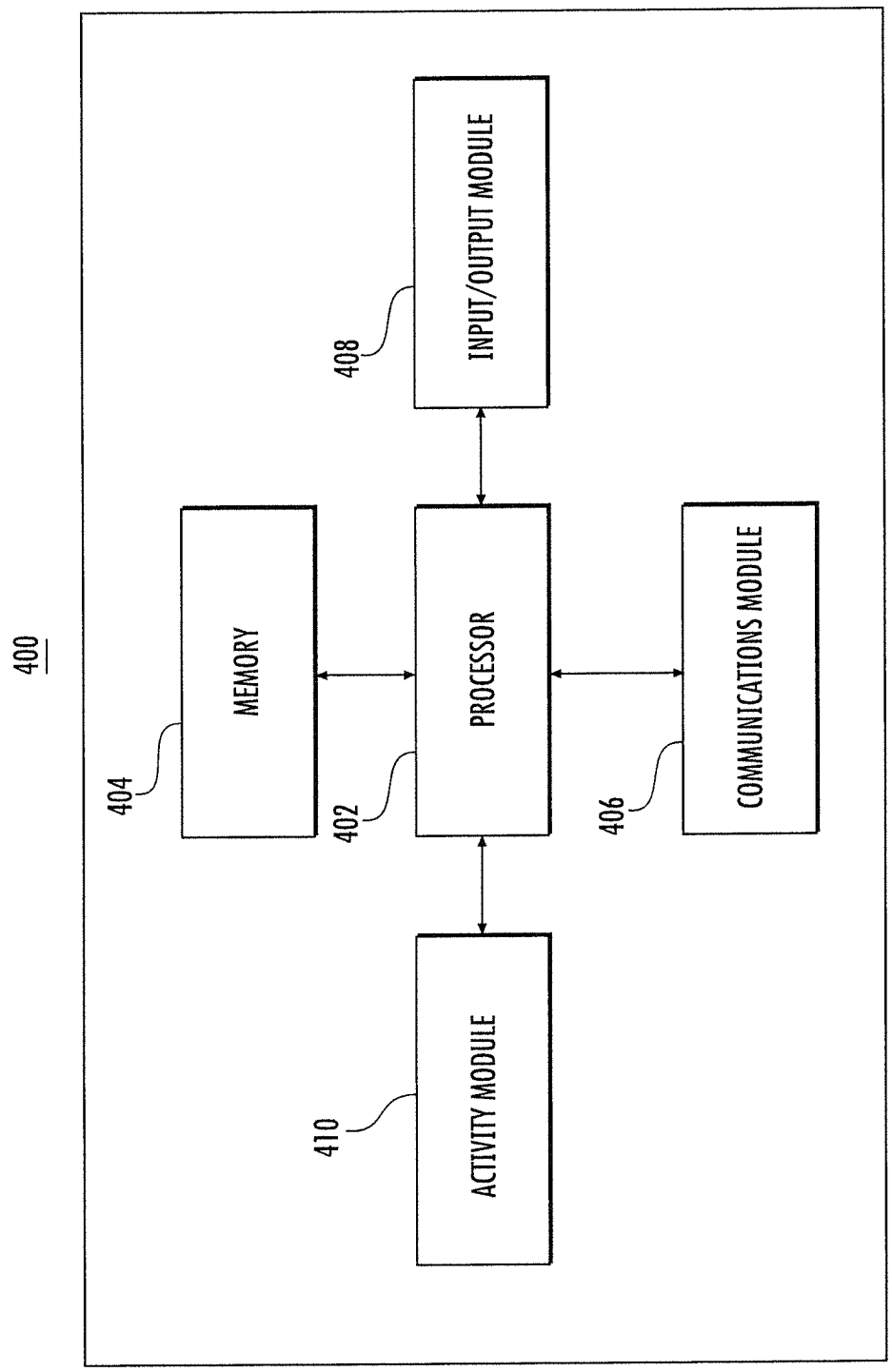
Figure 5:
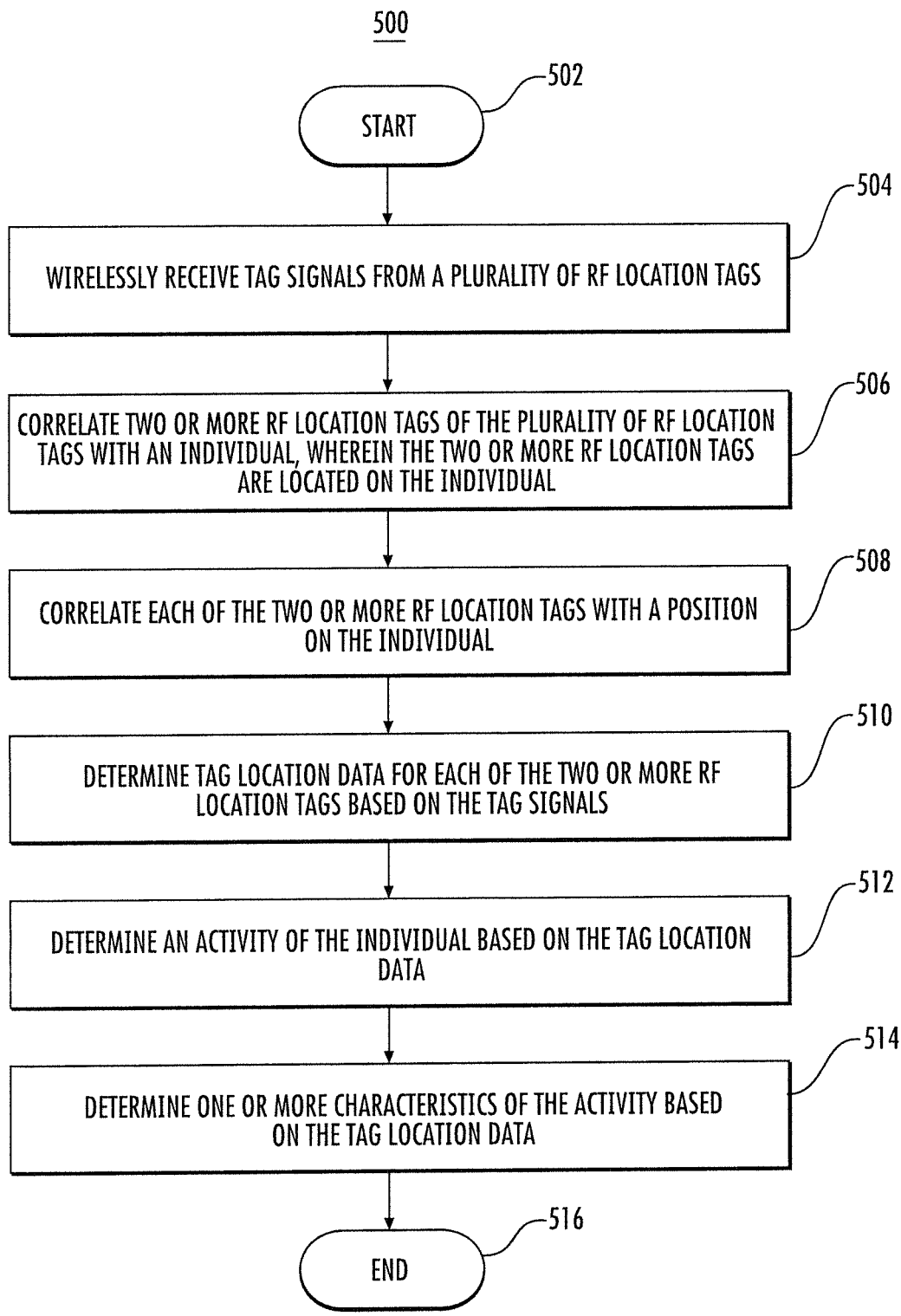
Figure 6:
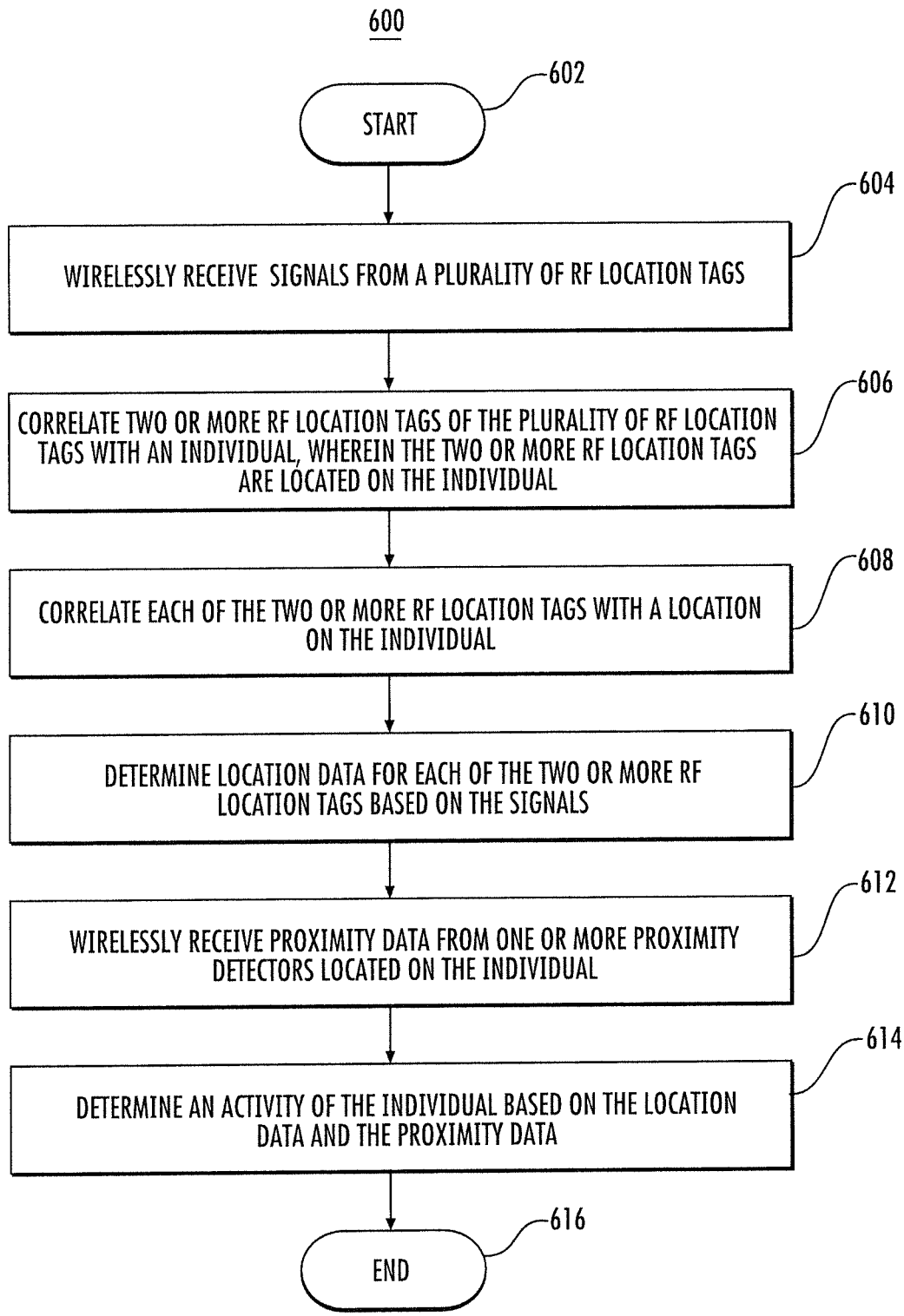
Figure 7:
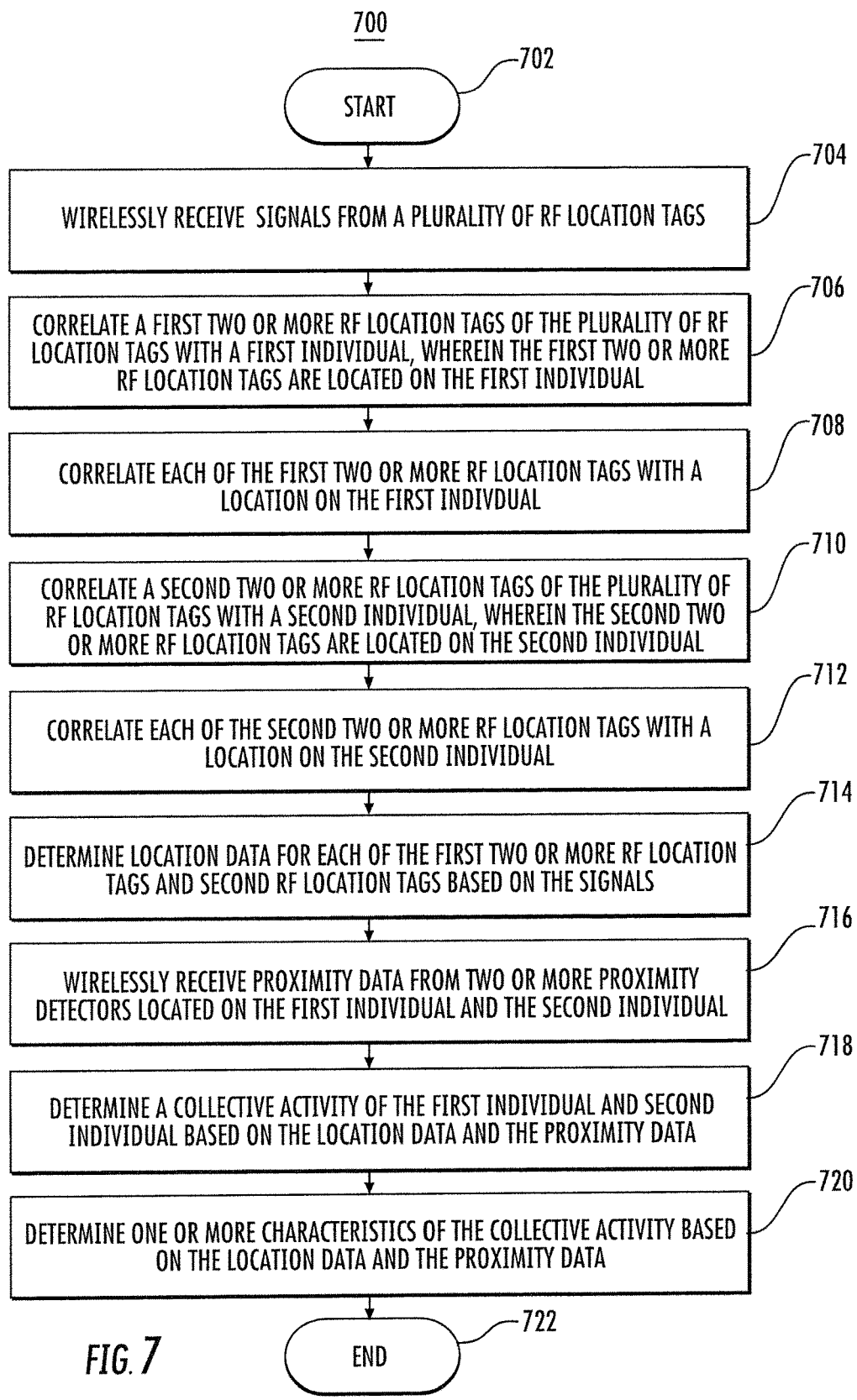

Having thus described some embodiments in general terms, reference will now be made to the accompanying drawings, which are not necessarily drawn to scale, and wherein:

FIG. 1 shows a block diagram of an example RF system, in accordance with some embodiments;

FIGS. 2 and 3 show example arrangements of tags on an individual, in accordance with some embodiments;

FIG. 4A shows a block diagram of an example receiver processing and analytics system, in accordance with some embodiments;

FIG. 4B shows an example schematic block diagram of circuitry, configured in accordance with some embodiments;

FIG. 5 shows a flowchart of an example method for determining an activity of an individual, performed in accordance with some embodiments;

FIG. 6 shows a flowchart of an example method for determining an activity of an individual based on proximity data, performed in accordance with some embodiments; and FIG. 7 shows a flowchart of an example of a method for determining an activity (or collective activity) involving two or more individuals, performed in accordance with some embodiments.

DETAILED DESCRIPTION

Embodiments will be described more fully hereinafter with reference to the accompanying drawings, in which some, but not all embodiments contemplated herein are shown. Indeed, various embodiments may be implemented in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information" and similar terms may be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, and/or the like.

BRIEF OVERVIEW

Methods, apparatus and computer program products described herein are operable for determining the activities and their characteristics for one or more individuals. Some embodiments may provide for an RF system configured to remotely monitor, in real-time, a plurality of individuals within a predetermined area, such as football players playing football within a football field. The term "individual" as used herein may refer to a person, patient, athlete, an animal, a machine (e.g., a race car), or other entity.

In some embodiments, radio frequency (RF) location tags, e.g., ultra-wideband (UWB) tags, and/or sensor, e.g., near field communication (NFC) sensor may be placed on each individual being monitored. For example, the RF location tags and/or sensors may be located within the equipment or under the clothing of the individuals so as to be visually unobservable. In some embodiments, the RF location tags and/or sensors may be located on individuals in a fashion that at least partially defines a human frame. For example, the RF location tags and/or sensors may be located at relevant joints, extremities and/or appendages of the individuals. Signals from the RF location tags and/or sensors may be received by receivers located about the predetermined area. Tag location data indicating the location of the tags may be determined (e.g., in real-time and/or over periods of time) to "reconstruct" the human frame and its motion. Based on the tag location data, among other things (e.g., sensor derived data transmitted by sensors indicating contact between individuals, objects (e.g., a football) and the environmental (e.g., the sidelines of a football field)), activities of the individuals (e.g., running, jumping, throwing tackling) and their characteristics (e.g., speed, momentum, hit power, etc.) may be programmatically determined, analyzed and reported.

Exemplary System Architecture

FIG. 1 illustrates a radio frequency locating system useful for determining the location of an individual (e.g. a football player on a football field) by determining RF location tag 102 (e.g., a ultra-wide band (UWB) location tag) location information at each receiver 106 (e.g., UWB reader, etc.); a timing reference clock to synchronize the frequency of counters within each receiver 106; and, in some examples, a reference tag 104, preferably a UWB transmitter, positioned at known coordinates to enable phase offset between counters to be determined. The systems described herein may be referred to as either "multilateration" or "geolocation" systems; terms which refer to the process of locating a signal source by solving for the mathematical intersection of multiple hyperbolae determined by the difference of arrival times of a signal received at multiple receivers.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose time-of-flight can be accurately determined using detection circuitry, such as in the receivers 106, which can trigger on the leading edge of a received waveform. In some examples, this short pulse characteristic allows necessary data to be conveyed by the system at a higher peak power, but lower overall power levels, than a wireless system configured for high data rate communications, yet still operate within local regulatory requirements which may limit overall power levels.

In some examples, the tags 102 may operate with an instantaneous −3 dB bandwidth of approximately 400 MHz and an average transmission rate below a 187.5 kHz regulatory cutoff. In such examples, the predicted maximum range of the system, operating at 6.0 GHz, is roughly 311 meters. Such a configuration advantageously satisfies constraints applied by regulatory bodies related to peak and average power densities (e.g., effective isotropic radiated power density), while still optimizing system performance related to range and interference. In further examples, tag transmissions with a −3 dB bandwidth of approximately 400 MHz yields, in some examples, an instantaneous pulsewidth of roughly 2.5 nanoseconds which enables a resolution to better than 30 centimeters.

Referring again to FIG. 1, the individual to be located has an attached RF location tag 102, preferably a tag having a UWB transmitter, that transmits a signal comprising a burst (e.g., 72 pulses at a burst rate of 1 Mb/s), and optionally, a burst having a tag data packet that may include tag data elements that may include, but are not limited to, a tag unique identification number (tag UID), other identification information, a sequential burst count, stored tag data, or other desired information for individual or personnel identification, inventory control, etc. In some embodiments, the tag data packet may include a tag-individual correlator that can be used to associate a specific individual with a specific tag. In some examples, the sequential burst count (e.g., a packet sequence number) from each tag 102 may be advantageously provided in order to permit, at a receiver hub 108, correlation of time of arrival (TOA) measurement data from various receivers 106.

In some examples, the RF location tag 102 may employ UWB waveforms (e.g., low data rate waveforms) to achieve extremely fine resolution because of their extremely short pulse (i.e., sub-nanosecond to nanosecond, such as a 2 ns (1 ns up and 1 ns down)) durations. As such, the tag data packet may be of a short length (e.g., 72-112 bits in some example embodiments), that advantageously enables a higher throughput and higher transmission rates. In some examples, higher throughput and/or higher transmission rates may result in larger datasets for filtering to achieve a more accurate location estimate. In some examples, rates of up to approximately 2600 updates per second can be accommodated without exceeding regulatory requirements. Alternatively or additionally, in some examples, the length of the tag data packets, in conjunction with other system functionality, may also result in a longer battery life (e.g., a 3.0 v 1 A-hr lithium cell battery may result in a tag battery life in excess of 3.8 years).

In some examples, one or more other tags, such as a reference tag 104, may be positioned within and/or about a monitored area, such as monitored area 100 illustrated herein as a football field. In some examples, the reference tag 104 may be configured to transmit a signal that is used to measure the relative phase (e.g., the count of free-running counters) of non-resettable counters within the receivers 106.

One or more (preferably four or more) receivers 106 are also at locations with predetermined coordinates within and/or around the monitored area 100. In some examples, the receivers 106 may be connected in a "daisy chain" fashion to advantageously allow for a large number of receivers 106 to be interconnected over a significant monitored area in order to reduce and simplify cabling, reduce latency, provide power and/or the like. Each of the receivers 106 includes a receiver for receiving transmissions, such as UWB transmissions, and preferably, a packet decoding circuit that extracts a time of arrival (TOA) timing pulse train, transmitter ID, packet number and/or other information that may have been encoded in the tag transmission signal (e.g., material description, sensor data, personal information, etc.) and is configured to sense signals transmitted by the tags 102 and one or more reference tags 104 (if present).

Each receiver 106 includes a time measuring circuit that measures time differences of arrival (TDOA) of tag bursts. The time measuring circuit is phase-locked (e.g., phase differences do not change and therefore respective frequencies are identical) with a common digital reference clock signal distributed via cable connection from a receiver hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog, signals are transmittable to the receiver hub 108. Advantageously, because packet data and measurement results can be transferred at high speeds to a receiver memory, the receivers 106 can receive and process tag (and corresponding individual) locating signals on a nearly continuous basis. As such, in some examples, the receiver memory allows for a high burst rate of tag events (i.e., tag data packets) to be captured.

Data cables or wireless transmissions may convey measurement data from the receivers 106 to the receiver hub 108 (e.g., the data cables may enable a transfer speed of 2 Mbps). In some examples, measurement data is transferred to the receiver hub at regular polling intervals.

As such, the receiver hub 108 determines or computes tag location (i.e., individual location) by processing TDOA measurements related to multiple data packets detected by the receivers 106. In some example embodiments, the receiver hub 108 may be configured to resolve the coordinates of a tag using nonlinear optimization techniques. The receiver hub 108 may also be referred to herein as a locate engine or a receiver hub/locate engine.

In some examples, the system described herein may be referred to as an "over-specified" or "over-determined" system. As such, the receiver hub 108 may then calculate one or more valid (i.e., most likely) locations based on a set of measurements and/or one or more incorrect (i.e., less likely) locations. For example, a location may be calculated that is impossible due the laws of physics (e.g., a tag on a football player that travels more than 100 yards in 1 second) or may be an outlier when compared to other determined locations. As such one or more algorithms or heuristics may be applied to minimize such error.

One such algorithm for error minimization, which may be referred to as a time error minimization algorithm, may be described as $$\varepsilon = \left\{ \sum_{j=1}^{N} \sum_{k=j+1}^{N} \left\{ (t_j - t_k) - \frac{1}{c} \left[ [(x-x_j)^2 + (y-y_j)^2 + (z-z_j)^2]^{\frac{1}{2}} - [(x-x_k)^2 + (y-y_k)^2 + (z-z_k)^2]^{\frac{1}{2}} \right] \right\}^2 \right\}$$

where N is the number of receivers, c is the speed of light, $x_{j,k}$, $y_{j,k}$ and $z_{j,k}$ are the coordinates of the receivers and $t_{j,k}$ are the arrival times received at each of the receivers. Note that only time differences may be received at receiver 106 in some example embodiments. The starting point for the minimization is obtained by first doing an area search on a coarse grid of x, y and z over an area defined by the user. This is followed by a localized steepest descent search.

Another or second algorithm for error minimization, which may be referred to as a distance error minimization algorithm, may be defined by:

$$\varepsilon = \sum_{j=1}^{N} \left[ [(x-x_j)^2 + (y-y_j)^2 + (z-z_j)^2]^{\frac{1}{2}} - c(t_j - t_0) \right]^2$$

where time and location differences are replaced by their non-differential values by incorporating an additional unknown dummy variable, $t_0$, which represents an absolute time epoch. The starting point for this algorithm is fixed at the geometric mean location of all active receivers. No initial area search is needed, and optimization proceeds through the use of a Davidon-Fletcher-Powell (DFP) quasi-Newton algorithm in some examples.

In order to determine the coordinates of a tag (T), in some examples and for calibration purposes, a reference tag (e.g., reference tag 104) is positioned at a known coordinate position $(x_T, y_T, z_T)$.

In further example embodiments, a number N of receivers $\{R_j: j=1, \ldots, N\}$ (e.g., receivers 106) are positioned at known coordinates $(x_{R_j}, y_{R_j}, z_{R_j})$, which are respectively located at distances, such as:

$$d_{Rj} = \sqrt{(x_{R_j} - x_T)^2 + (y_{R_j} - y_T)^2 + (z_{R_j} - z_T)^2}$$

from a reference tag.

Each receiver $R_j$ utilizes, for example, a synchronous clock signal derived from a common frequency time base, such as clock generator. Because the receivers are not synchronously reset, an unknown, but constant offset $O_j$ exits for each receiver's internal free running counter. The value of the offset $O_j$ is measured in terms of the number of fine resolution count increments (e.g., a number of nanoseconds for a one nanosecond resolution system).

The reference tag is used to calibrate the radio frequency locating system as follows:

The reference tag emits a signal burst at an unknown time $\tau_R$. Upon receiving the signal burst from the reference tag, a count $N_{R_j}$ as measured at receiver $R_j$ is given by $$N_{R_j} = \beta \tau_R + O_j + \beta d_{Rj}/c$$

where c is the speed of light and $\beta$ is the number of fine resolution count increments per unit time (e.g., one per nanosecond) Similarly, each individual tag $T_i$ of each individual to be located transmits a signal at an unknown time $\tau_i$ to produce a count $$N_{ij} = \beta \tau_i + O_j + \beta d_{ij}/c$$

at receiver $R_j$ where $d_{ij}$ is the distance between the individual tag $T_i$ and the receiver at receiver $R_j$. Note that $\tau_i$ is unknown, but has the same constant value for receivers of all receivers $R_j$. Based on the equalities expressed above for receivers $R_j$ and $R_k$ and given the reference tag information, differential offsets expressed as differential count values are determined as follows:

$$N_{R_j} - N_{R_k} = (O_j - O_k) + \beta \left( \frac{d_{R_j}}{c} - \frac{d_{R_k}}{c} \right)$$

or $$(O_j - O_k) = (N_{R_j} - N_{R_k}) - \beta \left( \frac{d_{R_j}}{c} - \frac{d_{R_k}}{c} \right) = \Delta_{jk}$$

$\Delta_{jk}$ is constant as long as $d_{Rj} - d_{Rk}$ remains constant, (which means the receivers and tag are fixed and there is no multipath situation) and $\beta$ is the same for each receiver. Note that $\Delta_{jk}$ is a known quantity, since $N_{R_j}$, $N_{R_k}$, $\beta$, $d_{R_j}/c$, and $d_{R_k}/c$ are known. That is, the differential offsets between receivers $R_j$ and $R_k$ may be readily determined based on the reference tag transmissions. Thus, again from the above equations, for an individual tag $(T_i)$ transmission arriving at receivers $R_j$ and $R_k$:

$$N_{i_j}-N_{i_k}=(O_j-O_k)+\beta(d_{i_j}/c-d_{i_k}/c)=\Delta_{jk}+\beta(d_{i_j}/c-d_{i_k}/c)$$

or, $$d_{i_j}-d_{i_k}=(c/\beta)[N_{i_j}-N_{i_k}-\Delta_{jk}].$$

The process further includes determining a minimum error value $E_i$, for each individual tag $T_i$, according to the functional relationship:

$$E_i = \min_{(x,y,z)} \sum_j \sum_{k>j} \left[(d_{i_j} - d_{i_k}) - (dist(T_{x,y,z}, R_j) - dist(T_{x,y,z}, R_k))\right]^2$$

where $dist(T_{x,y,z}, R_j) = \sqrt{(x_{R_j} - x)^2 + (y_{R_j} - y)^2 + (z_{R_j} - z)^2}$ is the Euclidean distance between point (x,y,z) and the coordinates of the $j^{th}$ receiver $R_j$. The minimization solution (x',y',z') is the estimated coordinate position for the $i^{th}$ tag at $t_0$.

In an example algorithm, this proceeds according to:

$$\varepsilon = \sum_{j=1}^{N} \left[[(x-x_j)^2 + (y-y_j)^2 + (z-z_j)^2]^{\frac{1}{2}} - c(t_j - t_0)\right]^2$$

where each arrival time, $t_j$, is referenced to a particular receiver (receiver "1") as follows:

$$t_j = \frac{1}{\beta}(N_j - N_1 - \Delta_{j_k})$$

and the minimization is performed over variables (x, y, z, $t_0$) to reach a solution (x', y', z', $t_0$').

In some example embodiments, the location of a tag 102 (e.g., tag location data) may then be output to the receiver processing and analytics system 110 for further processing to advantageously provide visualizations, predictive analytics and/or the like.

Tags on a Human Frame

FIG. 1 shows a monitored area 100. The monitored area 100 comprises a plurality of positions at one or more time epochs. The plurality of positions may be divided into one or more zones. Each zone may be described by one or more coordinate systems, such as a local NED (North-East-Down) system, a latitude-longitude system, or even a yard line system as might be used for an American football game. A location is a description of a position, or a plurality of positions, within the monitored area. For example, a field marker at the intersection of the south goal line and west out of bounds line at Bank of America Stadium in Charlotte, N.C. could be described as {0,0,0} in a local NED system, or 35.225336 N 80.85273 W longitude 751 ft. altitude on a latitude-longitude system, or simply "Panthers Goal Line" in a yard line system. Because different types of locating systems or different zones within a single locating system may use different coordinate systems, a Geographical Information System may be used to associate location data.

FIG. 2 shows an individual 200, e.g., a football player, equipped with an example arrangement of a plurality of RF location tags 202a-k, which may represent one set of tags 102 shown in FIG. 1. The plurality of RF location tags may be each located on individual 200 at locations such that the plurality of RF location tags fully or at least partially define a human frame. For example, RF location tags may be placed at joints and/or extremities of individual 200 that are of interest. As such, RF location tags 202a-k may provide robust location data for determining information concerning the body motion kinetics of individual 200.

For example, RF location tag 202a may be located at or near the head (e.g., within the helmet), RF location tags 202b and 202c may be located at or near the shoulders (e.g., under or proximate to each shoulder pad, respectively), RF location tags 202d and 202e may be located at or near the elbows (e.g., in each sleeve or elbow pad, respectively), RF location tags 202f and 202g may be located at or near the hands (e.g., in each glove or wrist brand, respectively), RF location tags 202h and 202i may be located at or near the knees (e.g., in each knee pad, respectively), and RF location tags 202j and 202k may be located at or near the feet (e.g., in each shoe, respectively). In some embodiments, one or more of RF location tags 202a-k may be affixed to the body of individual 200, such as by adhesive or perhaps as sewn into garments, or may be located on individual 200 using any other suitable techniques.

In some embodiments, reference body distance data between pairs of RF location tags 202a-k may be determined to facilitate dynamic determination of individual 200 from a plurality of individuals (e.g., as shown by each of tags 102 in FIG. 1). As shown in FIG. 2, for example, body distance 204 between RF location tag 202c and RF location tag 202e may be measured (e.g., the distance between the shoulder and elbow of individual 200) using conventional tools (e.g., tape measure, ruler, laser measurement tools, calipers, etc.) and stored as "reference body distance data" or a "reference body distance" for individual 200. Similarly, body distance data may be measured between other RF location tags of individual 200 as well as for RF location tags on each of the plurality of individuals (e.g., each player in uniform for a particular game). Such measured body distance data may be stored to one or more databases as reference body distance data as discussed herein. Reference body distance data is not strictly limited to distances and may include rotational data, vector-based data, pressure data, and other measured data associated with an individual.

In some embodiments, reference body distance data may be collected based on various anatomical measurements. For example, and without limitation, reference body distance data may include measurements taken between: an individual's left shoulder and his left elbow, an RF location tag worn proximate an individual's left shoulder and his left elbow, an RF location tag worn proximate an individual's left shoulder and an RF location tag worn proximate his left elbow, an individual's right shoulder and his right elbow, an RF location tag worn proximate an individual's right shoulder and his right elbow, an RF location tag worn proximate an individual's right shoulder and an RF location tag worn proximate his right elbow, and any other body part or RF location tag position that could be expected to remain consistent or produce repeatable distances over a defined period of time (e.g., one athletic season, one year, etc.).

In still other embodiments, reference body distance data may include a collection of measurements for each individual. For example, and without limitation, reference body distance data may include measurements between: an individual's shoulder (and/or shoulder mounted RF location tag) and elbow (and/or elbow mounted RF location tag), an individual's knee (and/or knee mounted RF location tag) and ankle (and/or ankle mounted RF location tag), and each of the individual's shoulders (and/or shoulder mounted RF location tags). In some embodiments, reference body distance data may include a collection of measurements for each individual taken with the individual oriented in various positions (e.g., standing, crouching, bent over, a three point stance, a runner's start position, or other position that may be relevant to a specific sport or other endeavor, etc.). For example, and without limitation, each of the measurements discussed above could be taken for an offensive lineman for a football team in a standing position, a three point stance position, and a prone position lying face down on the ground. Reference body distance data may further include pressure information related to a particular position or tensing of certain muscles of the individual.

Reference body distance data may also include positional data for an individual mapped to a GIS (Geographic Information System). For example, reference body distance data may include global positioning system (GPS) or differential GPS (DGPS) information that is mapped to a GIS.

In still other embodiments, reference body distance data may include RF signal strength information, which may vary by distance or proximity to a RF receiver. In one embodiment, at least one RF tag or sensor may be configured to include an RF receiver, which could then determine RF signal strength for other RF tags or sensors co-located on the individual. Such information may be stored as reference body distance data and used as discussed herein.

Reference body distance data may further include logical data such as true/false or on/off indications. For example, such logical data may be generated based on binary determinations as to whether one or more RF tags or sensors are disposed in a communicable range (e.g., a "1" might indicate yes while a "0" might indicate no).

In still other embodiments, reference body distance data may include aggregated measurements or statistical representations of such measurements. For example, and without limitation, multiple measurements may be taken for a single individual for each of the measurements discussed above. These measurements, along with an average, maximum, minimum, mode, or standard deviation of such measurements, may be stored to one or more databases as reference body distance data. Similarly, multiple measurements may be taken for a type or class of individuals (e.g., quarterbacks, left tackles, wide receivers, safeties, pitchers, left fielders, etc.) for each of the measurements discussed above. These measurements too, along with an average, maximum, minimum, mode, or standard deviation of such measurements, may be stored to one or more databases as reference body distance data.

As discussed above, each RF location tag may be a device configured for transmitting a signal, for example, a UWB signal that includes a TOA timing pulse (e.g., blink data), and optionally, a tag data packet that may include, but is not limited to, ID information (e.g., tag unique ID), a sequential burst count or other desired information. The tag signals may be collected and used, e.g., by the receiver hub 108 of FIG. 1, to determine tag location data at one or more times, which may in turn be used, e.g., by the receiver processing and analytics system 110 of FIG. 1, to determine location data and body motion kinetics of the tagged individual. The tag signal may include analog and/or digital data.

Tag location data may be determined for each RF location tags 202*a-k* based on the received tag signals (i.e., TOA timing pulses or blink data). Next, body distance data may be programmatically determined based on the tag location data (referred to herein as "determined body distance data" or a "determined body distance") and compared against the reference body distance data. More particularly, tag location data and sensor data may be used as appropriate to programmatically derive determined body distance data, which may then be compared against reference body distance data. Such dynamic associations between RF location tags and individuals may be advantageous, for example, because equipment (e.g., helmets, shoulder pads, etc.) including tags and/or tags themselves may be interchangeable and/or more conveniently replaced.

In one embodiment, determined body distance data may be compared against reference body distance data stored to one or more databases (e.g., role database 114 of FIG. 4A) to identify an individual (i.e., determine identity information and/or retrieving individual profile information). For example, a determined body distance of 23 inches between RF location tag 202*c* and 202*e* may correlate to corresponding reference body distance data. In another embodiment, multiple values of determined body distance data may be used to more precisely identify an individual (e.g., John Smith) and/or class of individual (e.g., quarterback). For example, ten previously tagged individuals may have a first determined body distance of 23 inches between RF location tags 202*c* and 202*e* but only one of those ten individuals may have a second determined body distance of 58 inches between RF location tags 202*c* and 202*k*, when determined in a standing, upright, position. In various embodiments, any determined body distance data may be stored to one or more databases. In still other embodiments, the above first determined body distance of 23 inches may be compared to a corresponding reference body distance (e.g., 23.34 inches) and the above second determined body distance of 58 inches may be compared to a corresponding reference body distance (e.g., 57.59 inches) to identify and individual or class of individual.

In some embodiments, one or more instances of determined body distance data may be stored to one or more databases as reference body distance data, which may then be available for comparison against future instances of determined body distance data. In other embodiments, one or more instances of determined body distance data may be stored with, or aggregated with, corresponding reference body distance data as a means for updating the reference body distance data.

As discussed above, each RF location tag 202*a-k* may be configured to transmit a wireless tag signal, such as a UWB signal, that includes a TOA timing pulse and/or additional information, such as tag data packets comprising individual identifying data, tag placement information, signal metadata (e.g., sequential burst count), or any other desired information. The tag signals from RF location tags 202*a-k* may be collected and used (e.g., by receiver hub 108 shown in FIG. 1) to determine tag location data such as tag locations and/or tag locations over time. Furthermore, similar techniques may be simultaneously applied to tags of other individuals (e.g., other players wearing tags 102 shown in FIG. 1) to determine their tag location data. Some or all of this tag location data, determined body distance data, and/or reference body distance data may be used (e.g., by the receiver processing and distribution system 110 shown in FIG. 1) to determine body motion kinetics and/or the activity of individual 200. For example, the tag location data, determined body distance data, and/or reference body distance data can be used to "reconstruct" the human frame of individual 200.

In another example, the individual may be equipped with two location tags, such as for example, a first RF location tag 202*b* proximate the chest or shoulder area and a second RF location tag 202k proximate the feet. A receiver processing and analytics system 110 may be configured to utilize data from the first RF location tag 202b and the second RF location tag 202k to determine if the individual is standing, squatting, crouching, lying on the ground, etc. For example, determined body distance data determined in connection with the first RF location tag 202b and the second RF location tag 202k may be compared with corresponding reference body distance data for the tagged individual. In one embodiment, determined body distance data need not be directly compared against corresponding reference body distance data for the actual tagged individual (i.e., data actually measured from a given individual). Rather, the determined body reference data may simply be compared to generally known anatomical statistics (e.g., the average distance between the shoulder and foot of a standing male is 4 fee, 8 inches, etc.) or anatomical statistics for a class of individuals (e.g., the average distance between the shoulder and foot of a standing male left tackle is 6 feet, 1 inch, etc.), which are also included among the reference body distance data referred to herein.

While FIG. 2 shows an example array of RF location tags 202a-k for individual 200, more or fewer RF location tags may be used. For example, where simple location of individual 200 is all that is desired (as opposed to information concerning the motion of arms, legs, or other tagged appendages), a single RF location tag may be used. The single RF location tag could be located at or near the individual's head, chest, torso, or the like. In another example, such as in the context of a soccer game, RF location tags may be placed at the feet, knees, etc., to track leg movements, while tags at the arms may not provide any relevant information and can be dropped. As would be apparent to one skilled in the art of tagging soccer individuals, RF location tags may be placed to track leg movements on some individuals, such as players, but placed on arms for some individuals, such as referees, or placed on both arms and legs for some individuals, such as goalies.

FIG. 3 shows an individual 300 wearing apparel equipped with an example arrangement of a plurality of RF location tags 302a-k and sensors 304a-k in accordance with some embodiments. The term "apparel" refers to one or more of the following: jersey or shirt, pants, helmet, pads, shoes, gloves, wristbands, socks, other athletic equipment, and the like. The term "appendage article" refers to any article that may be worn on or otherwise affixed to an appendage of an individual including, without limitation, a sock, a shoe, a shin guard, a knee pad, a glove, a wristband, an elbow pad, a head band, a necklace, a hat, a helmet, and the like. RF location tags 302a-k may be similar in function and/or placement as RF location tags 202a-k discussed above in connection with FIG. 2. As such, RF location tags 302a-k may represent one set of tags 102 shown in FIG. 1.

The term "sensor" as used herein refers to any device that detects, measures, indicates or records a parameter associated with an individual's motion, health, relative proximity to other individuals, or other environmental measurements. To clarify, the term "environmental measurements" includes measurements concerning the environment proximate the sensor including, without limitation, ambient information (e.g., temperature, position, humidity, etc.) and information concerning an individual's health, fitness, operation, and/or performance. Environmental measurements may be stored or transmitted in either analog or digital form and may be transmitted as individual measurements, as a set of individual measurements, and/or as summary statistics. For example, temperature in degrees Celsius may be transmitted as {31}, or as {33, 32, 27, 22, 20, 23, 27, 30, 34, 31}, or as {27.9}.

In the depicted embodiment, sensors 304a-k are proximity detectors. A "proximity detector" is a type of sensor that senses identity within an area (e.g., a local area) that is small with respect to the monitored area 100 of FIG. 1. An example proximity detector that is discussed in greater detail below in connection with some embodiments is a near field communication (NFC) sensor. While the examples discussed below refer to NFC sensors for illustration purposes, one of ordinary skill in the art will appreciate that the inventive concepts herein described are not limited to use with NFC sensors and may be applied to other proximity detectors and more generally to other types of sensors.

Near field communication is defined by a collection of standards for radio frequency communications that may be used when two devices are in close proximity. Protocols for implementation of near field communication may comply with industry standards, such as ISO/IEC 18092, published by the International Standards Organization. Typical ranges for near field communications are approximately four centimeters. Near field communications can support two-way (or peer-to-peer) communications between devices. In a passive mode, an NFC initiator device may output a carrier field that a target device (or transponder) uses to respond by modulating the provided field. In an active mode, the initiator and the target can each generate a carrier field, and the devices communicate by altering the fields. When utilizing two-way communications, two devices may exchange data to perform various functionalities that are enabled as a result of their near field communications.

Because near field communications require close proximity (e.g., no more than a few inches) to establish a communications link, the operation of establishing a link with another NFC device may be referred to as a "tap." The term "tap" as used herein does not necessarily refer to physical contact between communicating NFC devices but rather refers to positioning the NFC devices in sufficiently close proximity to establish an NFC communications link.

In the embodiment of FIG. 3, sensors 304a-k are NFC devices and shall be referred to hereafter, for simplicity, as NFC sensors 304a-k. The depicted sensors are proximity detectors and are configured to wirelessly communicate with other proximity detectors (e.g., NFC sensors) using near field communications. In some embodiments, each NFC sensor may also wirelessly (e.g., perhaps through a common transmitter) communicate proximity and/or touch/tap information (also referred to herein as a type of sensor derived data) to receivers 106, either directly or via RF location tags 302a-k.

In some embodiments, NFC sensors 304a-k may be each co-located (e.g., located at or near the same location) with respective ones of RF location tags 302a-k. Co-location of NFC sensors and RF location tags may allow an NFC sensor to communicate with a co-located RF location tag to transmit the sensor data generated by the NFC sensor. The RF location tag may then send the sensor data to receivers 106 using UWB signals. In some embodiments, regardless of whether the NFC sensors communicate directly with receivers 106 or via the RF location tags, sensor data from the NFC sensors may be communicated over the tag signals communications channel. In some embodiments, one or more hybrid sensor-RF location tags (e.g., NFC sensor or other type of sensor) may be used rather than co-located NFC sensors and RF location tags. In other embodiments, the NFC sensors may include separate UWB transmitters and as such may be located on individual 300 without a co-located RF location tag.

The distribution and location of NFC sensors and RF location tags on individual 300 may vary, such as depending on the context or the activity information desired. For example, individual 300 may be equipped with a plurality of NFC sensors that fully or at least partially defines a human frame while one or more RF location tags may be co-located on the individual with a respective one of the NFC sensors. In another example, at least one RF location tag and/or NFC sensor may be located on the individual without a corresponding co-located tag at or near the same location. In some embodiments, RF location tags may be placed at locations where body motion kinetics information is desirable (e.g., at the joints and/or on appendages of an individual) while NFC sensors may be placed at locations where NFC data (e.g., touch or proximity information) is desirable (e.g., at the hands, shoulder pads, feet in football, where contact at such locations may have a contextual significance).

Returning to FIG. 3, NFC sensor 304a may be located at or near the head (e.g., co-located with RF location tag 302a) in a first portion of the apparel (e.g., the helmet), NFC sensors 304b and 304c may be located at or near the shoulders (e.g., co-located with RF location tags 302b and 302c, respectively) in a second portion of the apparel (e.g., a shirt), NFC sensors 304d and 304e may be located at or near the elbows (e.g., e.g., co-located with RF location tags 302d and 302e, respectively) in a third portion of the apparel (e.g., appendage articles, namely, elbow pads), NFC sensors 304f and 304g may be located at or near the hands (e.g., co-located with tags UWB 302f and 302g, respectively) in a fourth portion of the apparel (e.g., appendage articles, namely, gloves), NFC sensors 304h and 304i may be located at or near the knees (e.g., co-located with RF location tags 302h and 302i, respectively) in a fifth portion of the apparel (e.g., appendage articles, namely, knee pads), and NFC sensors 304j and 304k may be located at or near the feet (e.g., co-located with RF location tags 302j and 302k, respectively) in a sixth portion of the apparel (e.g., appendage articles, namely, shoes).

In some embodiments, each of NFC sensors 304a-k may communicate with each other or with other NFC sensors (e.g., as may be placed on other individuals, individuals, and/or locations) when at least two NFC sensors are brought within close proximity. As such, some embodiments may use NFC sensors for finer activity determination than may be possible with only RF location tags. For example, two NFC sensors may be configured to communicate only when they are separated by a few centimeters and as such may be leveraged to more precisely determine that two individuals have made contact. As shown in FIG. 3, NFC sensor 306 may be placed on football 308 such that it may be determined that individual 300 is carrying football 308 when, for example, NFC sensor 306 is within communicable range with (i.e., in close proximity to) NFC sensor 304f and/or 304g at or near the hand of individual 300. In some embodiments, football 308 may further include a RF location tag configured to communicate with receiver 106.

In some embodiments, one or more NFC sensors may be placed at or near locations in the predetermined area, such as football field 101 shown in FIG. 1. For example, NFC sensors may be located at or near a boundary (e.g., goal line, first down line, sideline, etc.) to determine the location of individual 300 with respect to the boundary. As shown in FIG. 3, NFC sensors 312 may be located near sideline 314 such that when NFC sensors 304j or 304k come within a communicable range of NFC sensors 312, individual 300 may be determined to have stepped out of bounds. In another example, NFC sensors may be placed at or near the goal line such that a touchdown may be determined when individual 300 is both carrying football 308 (e.g., based on location data of an RF location tag associated with the football) and at least one of NFC sensors 304a-k are within communicable range of the NFC sensors at or near the goal line (e.g., signifying that a part of individual 300 has broken the threshold of the goal line).

In some embodiments, one or more NFC sensors and RF location tags may share a single communications channel for communication with receivers 106, such as a single UWB transmitter configured to wirelessly transmit signals as discussed above. For example, each of NFC sensors 304a-k and RF location tags 302a-k may share a single UWB transmitter. In another example, each co-located pair of NFC sensors and RF location tags may share a UWB transmitter. In yet another example, each NFC sensor and RF location tag may include its own UWB transmitter for communication with receivers 106. When two or more tags share a common transmitter, the transmitter may be configured to buffer and/or transmit signals for the tags, such as when the transmitter is interrogated by receivers 106 and/or at predetermined times (e.g., regular intervals). In some embodiments, one or more NFC sensors may be disposed in wired or wireless communication with one or more RF location tags and, thus, may leverage the transmitters of the one or more RF location tags to package and relay data to receivers 106.

In some embodiments, one or more NFC sensors and RF location tags may also share a common power supply, such as power supply 310 shown in FIG. 3. Power supply 310 may be disposed in electrical communication (e.g., through wires sewn into clothing, using electrically conductive fabric, etc.) with the RF location tags 302a-k and NFC sensors 304a-k to provide primary and/or back-up power. In the depicted embodiment, power supply 310 is mounted within a pocket (not shown) defined in the breastplate of the depicted player's shoulder pads.

In some embodiments, RF location tags 302a-k and/or NFC sensors 304a-k may receive primary and/or backup power from the heat and/or moisture generated by individual 300. For example, heat or moisture may be used to provide primary power, while a power supply (e.g., one or more batteries) may be used to provide backup power.

In some embodiments, as referenced above, various sensors may additionally and/or alternatively include a sensor other than a proximity detector (i.e., a NFC sensor). For example, one or more sensors may be an eye dilation sensor (e.g., positioned in glasses or a visor proximate to the eyes); a hydration sensor configured to monitor sweat loss or sweat loss rate (e.g., positioned in a body suit or shirt proximate the back); a heat sensor; an accelerometer for measuring acceleration; an environmental sensor for measuring environmental measurements such as outside temperature, humidity, barometric pressure, wind speed, air quality or composition; a heart rate censor; a blood pressure monitor; a blood chemistry sensor configured for monitoring levels of one or more of carbon dioxide, oxygen, potassium, calcium, sodium, hematocrit, temperature and pH, etc.

Another type of sensor is a triangulation positioner. A "triangulation positioner" is a type of sensor that senses position. In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included among sensor derived data as environmental measurements.

In another embodiment, a triangulation positioner comprises one or more cameras or image-analyzers that receive emitted or reflected light or heat, and then analyzes the received images to determine the location of an individual or sensor. Although a triangulation positioner may transmit data wirelessly, it is not a RF location tag because it does not transmit a TOA timing pulse or a tag signal that can be used by a receiver hub 108 to calculate location. In contrast, a triangulation positioner senses position and computes a position calculation that may then be used as environmental measurements by the receiver hub 108 to enhance or improve its tag location data.

Each of the above referenced sensors may be co-located with an RF location tag or may be located elsewhere on the human frame. As such, one or more sensors may provide sensor derived data for monitoring health, fitness, operation and/or performance, which is also referred to herein as health data. In some embodiments, sensor derived data from any type of sensor may leverage communications over the tag signal communication channel (e.g., a UWB communications channel), such as to receivers 106. In that sense, the system may be configured to backhaul some or all sensor data over the tag signal (e.g., UWB) communications channel.

Data derived or extracted from tag signals transmitted from one or more RF location tags is referred to herein as "tag derived data" and shall include, without limitation, tag data, tag UID, tag-individual correlator (i.e., data that indicates a correlation to a specific individual), tag-sensor correlator (i.e., data that indicates a correlation to a specific RF location tag), tag data packets, blink data, time measurements (e.g. time of arrival, time difference of arrival, phase), signal measurements (e. g., signal strength, signal direction, signal polarization, signal phase), determined body distance data, and tag location data (e.g., including tag location estimates). Information or data derived or extracted from sensor signals transmitted from one or more sensors is referred to herein as "sensor derived data" and shall include, without limitation, sensor UID, additional stored sensor data, sensor-individual correlator (i.e., data that indicates a correlation to a specific individual), environmental measurements, sensor information packets, position calculations (including sensor position estimates), position information, identity information, tag-sensor correlator (i.e., data that indicates a correlation to a specific RF location tag), and associated sensor data. Data derived or extracted from stored individual data is referred to herein as "individual profile information" and shall include, without limitation, tag-individual correlator, sensor-individual correlator, identity information, name, uniform number and team, biometric data, tag position on individual, role (e.g., running back), age, height, and weight, reference body distance data, stored tag, sensor, or individual velocity information, stored tag, sensor, or individual acceleration information, etc. In various embodiments, the receiver hub 108 may transmit tag derived data, sensor derived data, individual profile information, and various combinations thereof to the receiver processing and analytics system 110.

FIG. 4A shows a block diagram of an example receiver processing and analytics system 110, in accordance with some embodiments. Receiver hub 108 may be configured to receive data (e.g., tag derived data, sensor derived data, individual profile information, reference tag data, etc.) from one or more receivers 106. In some embodiments, receiver hub 108 may access or provide a data transmission link to each of one or more receivers 106 in succession and download data buffered in receivers 106 (e.g., as received by receivers 106 since receiver hub 108 last accessed the data at receivers 106).

Receiver hub 108 may further be configured to determine tag location data for each of RF location tags 102 by processing the TOA measurement data (and reference tag data, when applicable) received from receivers 106 and provide the tag location data to receiver processing and analytics system 110. In some embodiments, receiver processing and analytics system 110 may include data filter 112 configured to receive tag location data and/or sensor data from the receiver hub 108.

Data filter 112 may be configured to associate the location data and/or sensor data to a particular individual using role database 114. A particular player may be associated with identifying data (e.g., individual profile information) such as a unique identifier, name, role (e.g., as a quarterback), jersey number or the like and the tag location data and/or sensor derived data may be associated with the identifying data. As such, role database 114 may be populated with information for RF location tags and/or sensors that are correlated to particular individuals and/or with particular positions on individuals where the tags/sensors are placed.

In some embodiments, the tags may be configured to transmit a tag identifier (e.g., tag UID) that may be associated with individual profile information, which includes, without limitation, tag placement data (i.e., tag position on individual), etc., in role database 114. In some embodiments, the RF location tags may transmit individual profile information or other identifying data and/or tag placement data rather than a tag identifier. In some embodiments, individual role database 114 may further include individual profile information that may be retrieved based on data from the tags, such as a tag identifier, individual identifying data and/or tag placement data. Alternatively and/or additionally, in some embodiments, reference body distance data may be stored in role database 114. Here, the tags may be configured to transmit tag identifiers that may be dynamically associated with a particular individual based on comparing determined body distance data calculated based on the locations of the RF location tags to reference body distance data of each individual being monitored. The reference body distance data, for example, may also be stored in role database 114.

In some embodiments, data filter 112 may be further configured to send tag location data, other tag derived data, and sensor derived data to respective engines configured to process each type of data. For example, tag location data may be sent to dynamics/kinetics engine 120 and sensor derived data may be sent to sensor data engine 116.

Sensor data engine 116 may be configured to receive the sensor derived data from data filter 112. Sensor data engine 116 may be configured to process the sensor derived data, such as proximity data, accelerometer data, proximity data, health sensor data, etc. For example, sensor data engine 116 may be configured to process proximity data to determine which NFC sensors are within near field communicable range, within close proximity, and/or in contact. Sensor data engine 116 may also process accelerometer data to determine the acceleration of various parts of the human frame. By locating accelerometers at various locations of interest on the individual (e.g., as shown in FIG. 3), sensor data engine 116 may estimate the acceleration of individual body parts. For example, the acceleration of a quarterback's arm may be estimated using sensor 304f shown in FIG. 3, even when the quarterback's body remains stationary overall. In another example, sensor data engine 116 may be configured to determine the health of the individual based on the received health data.

In some embodiments, sensor data engine 116 may be configured to access sensor data models database 118 to receive reference (e.g., historical and/or contextual) sensor data. For example, the reference sensor data may include reference proximity data indicating contextually significant proximity data. Proximity data indicating that NFC sensor 306 of football 308 is in close proximity to NFC sensor 304f (e.g., at the hand of individual 300) may have a contextual significance because individual 300 may be determined to be the ball carrier. As such, reference proximity data may indicate that the football being at the individual's hands should be stored, analyzed or otherwise processed while proximity data indicating the football being near an individual's elbow may be discarded. In other examples, reference proximity data may indicate a contextual significance of an individual making contact with a second individual (e.g., hands, shoulders, etc. to another's body) or a location (e.g., stepping out of bounds). In that sense, sensor derived data and reference sensor data may be used to provide finer determination of activities than may be possible using only tag location data.

In some embodiments, the reference sensor data may further include reference health data related to the health of the individual or similarly situated individuals (e.g., other football players, quarterbacks, patients, runners, etc.). For example, the reference health data may be generated from capturing data from the individual equipped with sensors and/or tags. Alternatively and/or additionally, the reference health data may be input to sensor data models database 118, such as by a user input device. Sensor data models database 118 may, additionally or alternatively, be populated with expected and/or normal health values of the individual or similarly situated individuals. For example, the health data may indicate that a particular blood pressure level is unhealthy.

In some embodiments, the reference health data may include different values that depend on the activity being performed. For example, an individual's healthy heart rate while running may be higher than while walking. As such, the reference health data may further be captured from the individual equipped with sensors and/or tags while performing various activities and may be stored in association with indications of various actions. In some embodiments, the reference health data may include different values depending on environmental factors. For example, an individual's healthy sweat loss rate may be higher for a higher temperature than for a lower temperature. As such, the reference health data may further be captured from the individual equipped with sensors and/or tags in different environmental conditions and/or while performing various activities and may be stored in association with indications of environmental conditions and/or actions.

In some embodiments, sensor data engine 116 may be configured to aggregate the sensor derived data received from the sensors over a period of time, such as over a play, a series of plays, a quarter, or a football game. For example, aggregated proximity data may indicate that a receiver has secured possession of the football after a catch. In another example, differences in acceleration data for multiple plays may indicate that a player is tired and needs to be substituted.

Receiver processing and analytics system 110 may be configured to monitor, track, and/or store the sensor data. For example, sensor data engine 116 may be configured to track aggregated proximity data, acceleration data and/or health data over time. In another example, sensor data engine 116 may be configured to provide sensor data of interest or contextual significance, such as to activity engine 124 or some other suitable computing device, such as a computing device and/or display device of a trainer, medical staff, coach, broadcaster, doctor, or the like.

Dynamics/kinetics engine 120 may be configured to receive the tag location data from data filter 112. In general, dynamic/kinetics engine 120 may be configured to determine activity data for the individual based on the tag location data. For example, the activity data may indicate an action of the individual (e.g., walking, running, catching, jumping, tackling, carrying a ball, etc.), characteristics of the activity (e.g., speed, acceleration, movement path over time, tackling power, force of a hit, timing of a tackle, etc.), the location of the individual with respect to the predetermined area (e.g., in-bounds, out-of bounds, in the end zone, outside of the end zone, past a first down marker, etc.), and/or the kinetic health of the individual (e.g., running or walking gait patterns), or the like.

As discussed above, the tag location data for an individual may be individually determined for each RF location tag located on the individual to at least partially define a human frame, such as for each of RF location tags 302a-k on individual 300 in FIG. 3. Advantageously, dynamics/kinetics engine 120 may use this tag location data to differentiate between a larger variety of activities of the individual than may be otherwise possible (e.g., by using only a single RF location tag).

In some embodiments, dynamics/kinetics engine 120 may further be configured to determine the activity data by comparing received tag location data with reference (e.g., historical and/or contextual) location data related to the individual and/or similarly situated individuals. The reference location data may be stored in dynamics/kinetics models database 122 and may be generated from capturing data from one or more individuals equipped with tags or sensors. As such reference location data may be stored with an indication of an associated action. Additionally and/or alternatively, the reference location data may be input to dynamics/kinetics models database 122 via a user input device.

In some embodiments, dynamics/kinetics engine 120 may be configured to send the activity data, such as to a computing device and/or display device of a trainer, medical staff, coach, broadcaster, doctor, or the like, or alternatively selected data of interest. Additionally and/or alternatively, dynamics/kinetics engine 120 may be configured to send aggregate activity data (e.g., a path of a wide receiver during every play of football game) and/or send selected activity data of interest.

In some embodiments, dynamics/kinetics engine 120 and sensor data engine 116 may be configured to communicate with each other (and/or with activity engine 124) to determine the activity data of the individual. For example, dynamics/kinetics engine 120 may indicate that an individual is running while sensor data engine 116 may indicate that the individual is holding the football. As such, the combination of tag location data and sensor derived data may indicate that the running individual is the ball carrier (e.g., as opposed to a blocker, defender, official, etc.).

In another example, whether health data of the individual is within a normal range may depend on the activity being performed, such as heart rate relative to walking or running. Furthermore, the activity being performed may indicate the health status of the individual. For example, a high momentum hit to the helmet determined by dynamics/kinetics engine 120 may indicate that the individual could be at risk for a concussion.

In some embodiments, receiver processing and analytics system 110 may further include activity engine 124. Activity engine 124 may be configured to determine collective activity data for a plurality of individuals (e.g., two or more individuals wearing tags 102 on football field 101 shown in FIG. 1). For example, the collective activity data may indicate the activity of a first individual with respect to a second individual (e.g., being hit, chased, blocked, facemask, etc.) or characteristics of that data (e.g., force of a collision). In another example, the collective activity data may indicate a formation of the offense or defense, a particular play being executed, whether a receiver was shoved out of bounds, or any other event involving multiple individuals and having contextual significance. As such, dynamics/kinetics engine 120 may be configured to determine activity data for each the plurality of individuals and send the activity data to activity engine 124. Additionally and/or alternatively, sensor data engine 116 may be configured to send relevant sensor derived data of each individual to activity engine 124. For example, activity engine 124 may be configured to determine the force of a tackle on a ball carrier.

In some embodiments, activity engine 124 may be configured to determine the occurrence of a particular event. Some example events, in the context of football, may include a pass attempt, an incomplete pass, a completed pass, passing yardage, a tackle, a sack, an injury, an offside or false start, a late hit, stepping out of bounds, a rush attempt, yards per rush, presence or absence from the field for a particular play, a potential injury, etc. In some embodiments, activity engine 124 may be configured to receive one or more reference event data from the sensor data engine 116, the dynamics/kinetics engine 120, or other historical reference data database (not shown) that may be used for comparison to determine the occurrence of the event. In some embodiments, the activity engine 124 may be further configured to receive reference event data to determine the occurrence of the event, such as from event data model database 126. For example, the reference event data may include associations of activity data and sensor derived data that indicate events of contextual significance.

In some embodiments, activity engine 124 may be configured to send event data indicating the determined event. The event data may be sent, for example, to a computing device or display device of an announcer, broadcast producer or technician (e.g., for a television broadcast), the coaching staff, medical staff, trainers, or the like. For example, event data may be sent to a computing device configured to record and/or analyze statistics of individuals (e.g., number of catches, number of carries, yards per carry, number of tackles, number of sacks, etc.). In some embodiments, an alert may be sent in response to a determination of a pre-defined event, unexpected event, and/or abnormal event. For example, an alert may be sent upon determining the individual has been injured or is otherwise unfit to remain in the game.

FIG. 4B shows a schematic block diagram of circuitry 400, some or all of which may be included in, for example, RF system 100, receivers 106, receiver hub 108 and/or receiver processing and analytics system 110. In accordance with some example embodiments, circuitry 400 may include various means, such as one or more processors 402, memories 404, communications modules 406, and/or input/output modules 408.

In some embodiments, such as when circuitry 400 is included in receiver processing and analytics system 110, activity module 410 may also or instead be included. As referred to herein, "module" includes hardware, software and/or firmware configured to perform one or more particular functions. In this regard, the means of circuitry 400 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 404) that is executable by a suitably configured processing device (e.g., processor 402), or some combination thereof.

Processor 402 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 4B as a single processor, in some embodiments, processor 402 may comprise a plurality of processors. The plurality of processors may be embodied on a single computing device or may be distributed across a plurality of computing devices collectively configured to function as circuitry 400. The plurality of processors may be in operative communication with each other and may be collectively configured to perform one or more functionalities of circuitry 400 as described herein. In an example embodiment, processor 402 may be configured to execute instructions stored in memory 404 or otherwise accessible to processor 402. These instructions, when executed by processor 402, may cause circuitry 400 to perform one or more of the functionalities related to activity determination as described herein.

Whether configured by hardware, firmware/software methods, or by a combination thereof, processor 402 may comprise an entity capable of performing operations according to embodiments of the present invention while configured accordingly. Thus, for example, when processor 402 is embodied as an ASIC, FPGA or the like, processor 402 may comprise specifically configured hardware for conducting one or more operations described herein. As another example, when processor 402 may be embodied as an executor of instructions, such as may be stored in memory 404, the instructions may specifically configure processor 402 to perform one or more algorithms, methods or operations described herein.

Memory 404 may comprise, for example, volatile memory, non-volatile memory, or some combination thereof. Although illustrated in FIG. 4B as a single memory, memory 404 may comprise a plurality of memory components. The plurality of memory components may be embodied on a single computing device or distributed across a plurality of computing devices. In various embodiments, memory 404 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 404 may be configured to store information, data, applications, instructions, or the like for enabling circuitry 400 to carry out various functions in accordance with example embodiments discussed herein. For example, in at least some embodiments, memory 404 may be configured to buffer input data for processing by processor 402. Additionally or alternatively, in at least some embodiments, memory 404 may be configured to store program instructions for execution by processor 402. Memory 404 may store information in the form of static and/or dynamic information. This stored information may be stored and/or used by circuitry 400 during the course of performing its functionalities.

Communications module 406 may be embodied as any device or means embodied in circuitry, hardware, a computer program product comprising computer readable program instructions stored on a computer readable medium (e.g., memory 404) and executed by a processing device (e.g., processor 402), or a combination thereof that is configured to receive and/or transmit data from/to another device, such as, for example, a second circuitry 400 and/or the like. In some embodiments, communications module 406 (like other components discussed herein) can be at least partially embodied as or otherwise controlled by processor 402. In this regard, communications module 406 may be in communication with processor 402, such as via a bus. Communications module 406 may include, for example, an antenna, a transmitter, a receiver, a transceiver, network interface card and/or supporting hardware and/or firmware/software for enabling communications with another computing device. Communications module 406 may be configured to receive and/or transmit any data that may be stored by memory 404 using any protocol that may be used for communications between computing devices. Communications module 406 may additionally or alternatively be in communication with the memory 404, input/output module 408 and/or any other component of circuitry 400, such as via a bus.

Input/output module 408 may be in communication with processor 402 to receive an indication of a user input and/or to provide an audible, visual, mechanical, or other output to a user. Input/output module 408 may include support, for example, for a keyboard, a mouse, a joystick, a display, an image capturing device, a touch screen display, a microphone, a speaker, a RFID reader, barcode reader, biometric scanner, and/or other input/output mechanisms. In embodiments wherein circuitry 400 may be implemented as a server or database, aspects of input/output module 408 may be reduced as compared to embodiments where circuitry 400 may be implemented as an end-user machine or other type of device designed for complex user interactions. In some embodiments (like other components discussed herein), input/output module 408 may even be eliminated from circuitry 400. Alternatively, such as in embodiments wherein circuitry 400 is embodied as a server or database, at least some aspects of input/output module 408 may be embodied on an apparatus used by a user that is in communication with circuitry 400. Input/output module 408 may be in communication with memory 404, communications module 406, and/or any other component(s), such as via a bus. Although more than one input/output module and/or other component can be included in circuitry 400, only one is shown in FIG. 4B to avoid overcomplicating the drawing (like the other components discussed herein).

In some embodiments, activity module 410 may also or instead be included and configured to perform the functionality discussed herein related to determining activities of individuals. In some embodiments, some or all of the functionality for activity determination may be performed by processor 402. In this regard, the example processes and algorithms discussed herein can be performed by at least one processor 402 and/or messaging module 410. For example, non-transitory computer readable storage media can be configured to store firmware, one or more application programs, and/or other software, which include instructions and other computer-readable program code portions that can be executed to control processors of the components of system 400 to implement various operations, including the examples shown above. As such, a series of computer-readable program code portions may be embodied in one or more computer program products and can be used, with a computing device, server, and/or other programmable apparatus, to produce the machine-implemented processes discussed herein.

Any such computer program instructions and/or other type of code may be loaded onto a computer, processor or other programmable apparatus's circuitry to produce a machine, such that the computer, processor other programmable circuitry that executes the code may be the means for implementing various functions, including those described herein. In some embodiments, one or more external systems (such as a remote cloud computing and/or data storage system) may also be leveraged to provide at least some of the functionality discussed herein.

As described above and as will be appreciated based on this disclosure, various embodiment may be configured as methods, mobile devices, backend network devices and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments have been described above with reference to block diagrams of components, such as functional modules, system components and circuitry. Below is a discussion of an example process flowcharts describing functionality that may be implemented by one or more components discussed above. Each block of the block diagrams and process flowcharts, and combinations of blocks diagrams and process flowcharts, respectively, can be implemented by various means including computer program instructions. These computer program instructions may be loaded onto a general purpose computer, special purpose computer, or other programmable data processing apparatus, such as processor 402, to produce a machine, such that the computer program product includes the instructions which execute on the computer or other programmable data processing apparatus create a means for implementing the functions specified in the flowchart block or block diagrams.

These computer program instructions may also be stored in a computer-readable storage device (e.g., memory 404) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the block diagrams and process flowcharts, and combinations of blocks in the block diagrams and process flowcharts, can be implemented by special purpose hardware-based computer systems that perform the specified functions or steps, or combinations of special purpose hardware and computer instructions.

Determining an Activity

FIG. 5 shows a flowchart of an example method 500 for determining an activity of an individual, performed in accordance with some embodiments. Method 500 is described herein as being performed by the example structures shown in FIGS. 1-4B for explanatory clarity. However, other suitable computing devices and/or contexts (e.g., non-football) may also be applicable in various embodiments.

Method 500 may begin at 502 and proceed to 504, where tag signals from a plurality of RF location tags may be wirelessly received. For example, the tag signals may be sent from RF location tags 102 and received by one or more receivers 106, as shown in FIG. 1.

At 506, two or more RF location tags of the plurality of RF location tags may be correlated with an individual, wherein the two or more RF location tags are located on the individual. As discussed above, the plurality of RF location tags may each send wireless signals that include a tag identifier and/or individual profile information (e.g., identifying data, tag-individual correlator, etc.) that may be used to determine the identity of the individual that is correlated with the two or more RF location tags.

In some embodiments, correlating the two or more RF location tags of the plurality of RF location tags with the individual may include correlating the two or more RF location tags with the individual from a plurality of individuals each having associated RF location tags. For example, the plurality of individuals may each include RF location tags 102 as shown in FIG. 1.

At 508, each of the two or more RF location tags may be correlated with a position on the individual. For example, the two or more RF location tags may be positioned on the individual such that the two or more RF location tags may fully or at least partially define a human frame. As such, at least one of the two or more RF location tags may be positioned at or near the individual's head, shoulder, elbow, wrist, knee, or foot. In some embodiments, RF location tags may be positioned on the individual as shown in FIGS. 2 and 3 for RF location tags 202a-k and RF location tags 302a-k, respectively.

In some embodiments, tag signals transmitted by the RF location tags may include tag placement data indicating a position on the individual where each of the two or more RF location tags is located and the correlation of RF location tags with positions on the individual may be determined based on the tag placement data.

At 510, tag location data for each of the two or more RF location tags may be determined based on the tag signals. For example, the two or more RF location tags may send UWB tag signals including TOA timing pulses to one or more UWB receivers, such as receivers 106 shown in FIG. 1. Furthermore, determining the tag location data may include determining an arrival time at the one or more UWB receivers for each of the signals. In some embodiments, the tag location data may be determined by a receiver hub or locate engine based on tag derived data from three or more receivers, such as via triangulation based on the arrival times of a common tag signal (e.g., from a single RF location tag) at each of the three or more receivers.

In some embodiments, associations between particular tags and individuals may be determined dynamically. For example, correlating the two or more RF location tags of the plurality of RF location tags with the individual may include receiving individual profile information (e.g., tag identifiers and/or tag placement data), determining tag location data for the two or more RF location tags, calculating determined body distance data for the two or more RF location tags (e.g., body distance 204 between RF location tag 202c and RF location tag 202e shown in FIG. 2) based on the tag location data, and comparing the determined body distance data against reference body distance data to determine the individual (i.e., identify the individual) from the plurality of individuals.

At 512, an activity of the person may be determined based on the tag location data. For example, the tag location data for each of the two or more RF location tags may be compared with reference location data stored in dynamics/kinetics model database 122, as shown in FIG. 4A. As discussed above, the reference location data may be associated with various activities or actions of the individual. As such, the tag location data for each RF location tag (e.g., including its correlation with locations on the individual) may be compared against the reference location data to determine the activity of the individual from a set of possible activities or actions of the individual such as walking, running, catching, jumping, tackling, etc.

For example, the individual may be determined to be running when the locations of RF location tags on the feet (e.g., RF location tags 302j and 302k shown in FIG. 3) change in a rapid, alternating pattern over time. In another example, the individual may be determined to be walking when the locations of the RF location tags on the feet change in a slower, alternating pattern over time. Virtually any type of activity or action of the individual may be determined and the set of possible activities from which the activity of the individual is selected may be chosen depending on context (e.g., football game, racing event, medical monitoring, etc.).

In general, tag location data of RF location tags may be measured over time to determine how far a particular tag moved, how far does a tag move in relation to another tag, how close are individual tags to each other, how fast does one tag move compared to another tag, etc.

At 514, one or more characteristics of the activity may be determined based on the tag location data. For example, if the individual is determined to be running, the individual's speed and/or acceleration may be determined based on the location of RF location tags versus time. The momentum of the individual may also be determined based on the speed and mass (e.g., weight) of the individual, which may provide an indication of tackling power. In another example, the movement path of the individual (e.g., a receiver's route)

may be determined based on the location of RF location tags over time. Other example characteristics of contextual relevance in football may include arm speed, leap height, agility (e.g. speed of direction changes), etc. Different characteristics may be determined in other contexts depending on their contextual significance. Method 500 may then end at 516.

FIG. 6 shows a flowchart of an example method 600 for determining an activity of an individual based on proximity data, performed in accordance with some embodiments. Method 600 is described herein as being performed by the example structures shown in FIGS. 1-4B for explanatory clarity. However, other suitable computing devices and/or contexts (e.g., non-football) may also be applicable in various embodiments.

Method 600 may begin at 602 and proceed to 604, where signals from a plurality of RF location tags may be wirelessly received. At 606, two or more RF location tags located on the individual of the plurality of RF location tags may be correlated with the individual. At 608, each of the two or more RF location tags may be correlated with a location on the individual. At 610, tag location data for each of the two or more RF location tags may be determined based on the tag signals. The discussion above at 504-510 of method 500 may be applicable to 604-610 of method 600.

At 612, proximity data from one or more proximity detectors (e.g., NFC sensors) located on the individual may be wirelessly received. As discussed above, the proximity data may indicate that the one or more proximity detectors is in near field communicable range (e.g., a few centimeters or less) with another proximity sensor, associated device, or other object such as may be located on a football (e.g., NFC sensor 306 on football 308 shown in FIG. 3) or at a boundary of a predetermined area (e.g., NFC sensor 312 located near sideline 314 shown in FIG. 3). Additionally and/or alternatively, the boundary may be a goal line, first down line, line of scrimmage, etc.

In some embodiments, the proximity detector may not be an NFC sensor but rather some other device configured to determine that an individual or other tagged object is in close proximity to (e.g., six inches or less) another object. Such proximity detectors may include an optical sensor, laser range finder, and the like.

In some embodiments, the proximity data may be wirelessly received via the same tag signals received from the RF location tags at 504. For example, NFC sensors and RF location tags may be co-located and/or share a common UWB transmitter. The NFC sensors may communicate proximity data with respective co-located RF location tags that transmit the proximity data with the wireless tag signal, such as over the UWB communications channel. In another example, hybrid sensor-RF location tags may be used rather than co-located NFC sensors and RF location tags.

At 614, an activity of the individual may be determined based on the tag location data and the proximity data. The discussion above at 514 of method 500 may be applicable at 614 of method 600. For example, the tag location data for each of the two or more RF location tags may be compared with reference location data stored in dynamics/kinetics model database 122, as shown in FIG. 4A. Similarly, the proximity data may be compared with reference proximity data stored in sensor data models database 118.

As discussed above, the proximity data may be used to provide additional indicators of the activity. For example, the proximity data may indicate that the individual is carrying the ball, such as when NFC sensor 306 on football 308 is within communicable range with NFC sensors 304f and/or 304g at or near the hand of individual 300, as shown in FIG. 3. In another example, NFC sensors 312 or other proximity detectors may be located near sideline 314 such that when NFC sensors 304j or 304k (e.g., at the feet of individual 300) comes within a communicable range of NFC sensor 312, individual 300 may be determined to be out of bounds. In another example, NFC sensors may be placed at or near the goal line such that a touchdown may be determined when individual 300 is both carrying football 308 and at least one of NFC sensors 304a-k are within communicable range of the NFC sensors at or near the goal line. Method 600 may then end at 616.

While method 600 is described with reference to proximity data and proximity detectors (e.g., NFC sensors), it is also applicable to other types of sensor data and other types of sensors that can be used to provide additional indicators of the activity.

FIG. 7 shows an example of a method 700 for determining an activity (or collective activity) involving two or more individuals, performed in accordance with some embodiments. Method 700 is described herein as being performed by the example structures shown in FIGS. 1-4B for explanatory clarity. However, other suitable computing devices and/or contexts (e.g., non-football) may also be applicable in various embodiments. Furthermore, method 700 is described for an activity involving two individuals, although similar techniques may be applicable to more than two or all of the individuals being monitored (e.g., as shown by each of RF location tags 102 in FIG. 1).

Method 700 may begin at 702 and proceed to 704, where tag signals from a plurality of RF location tags may be wirelessly received. At 706, a first two or more RF location tags of the plurality of RF location tags may be correlated with a first individual. For example, a tag-individual correlator may be stored to a role database indicating that the first two or more RF location tags may be positioned on (worn by) the first individual. At 708, each of the first two or more RF location tags may be correlated with a position on the first individual. The discussion above at 504-508 of method 500 may be applicable at 704-708. At 710, a second two or more RF location tags of the plurality of RF location tags may be correlated with a second individual. For example, the second tag-individual correlator made be stored to a role database indicating that two or more RF location tags may be positioned on the second individual. At 712, each of the second two or more RF location tags may be correlated with a position on the second individual. The discussion above at 506-508 of method 500 may also be applicable at 710-712, except with respect to the second individual. The first and second individuals may be further associated with teams, such as different teams or the same team. For example, an individual-team correlator may be stored to the role database for each individual.

At 714, tag location data for each of the first two or more RF location tags and second RF location tags may be determined based on the tag signals. The discussion above at 510 of method 500 may be applicable at 714.

At 716, proximity data from two or more proximity detectors (e.g., NFC sensors) positioned on the first individual and the second individual may be wirelessly received. The discussion above at 612 of method 600 may be applicable at 716. The proximity data may indicate, for example, that a part of the first individual has made contact with a part of the second individual (e.g., a first NFC sensor on the first individual is in near field communicable range with a second NFC sensor on the second individual). Furthermore, the proximity data may indicate that the first or second individual is carrying the ball and/or the location of the first or second individual relative to a predetermined area or location in the predetermined area (e.g., out of bounds of football field 101 shown in FIG. 1).

At 718, a collective activity of the first individual and second individual may be determined based on the tag location data and the proximity data. The discussion above at 512 of method 500 may be applicable at 718, such as to determine the activity of each of the second and first individuals. For example, the tag location data and proximity data for each of the first and second two or more RF location tags may be compared with reference location data and reference proximity data, respectively, stored in dynamics/kinetics model database 122 and sensor models database 118, as shown in FIG. 4A. Furthermore, the activities of the first and second individuals may be used to determine a collective activity, such as by comparing the location data and proximity data for the first and second individuals collectively with reference collective location data and proximity data, respectively.

Some example collective activities involving two or more individuals may include tackling, chasing, blocking, hits to specific locations (e.g., head blows), facemask penalties (e.g., using an NFC sensor placed at or near the facemask), or the like. For example, a first individual may be determined to be tackling a second individual when the second individual is determined to be carrying the ball, as described above, and when the first individual of a different team is determined to have made contact with the second individual. A successful tackle may be determined, for example, when tag location data and/or proximity data correlated to the second individual indicate that the second individual's knee(s), elbows, etc. are touching the ground following contact with the first individual. In another example, depending on the position and arrangement of the proximity detectors that registered the proximity data, the position/orientation of a hit may be determined. In another example, a tackle on a quarterback registered behind the line of scrimmage may be determined to be a sack. In that sense, the identity and/or role of individuals (e.g., team affiliation, position, etc.) may also be used to determine activities and/or their characteristics. As discussed above, the identity and/or role of individuals may be stored in role database 114 and referenced when suitable.

The nature of the collective activity as well as the corresponding location data and proximity data that indicate the collective activity may depend on the context, which in some embodiments, may be defined by reference collective location data and proximity data in dynamics/kinetics model database 122 and the sensor models database 118. Some other examples of collective activity may include formation of the offense or defense, a particular play being executed, whether a receiver was shoved out of bounds by a defender, or the like.

At 720, one or more characteristics of the collective activity may be determined based on the location data and proximity data. The discussion above at 514 of method 500 may be applicable at 720, such as to determine one or more characteristics of the activity of each of the second and first individuals. A characteristic of a collective activity may include tackling power or hit power. For example, the speed and direction (e.g., velocity) of the first and second individual may be determined based on the location data over time. As such, the momentum of a collision between the first and second individual may be determined based on the velocities and weights of the first and second individual. Method 700 may then end at 722.

While method 700 is described with reference to proximity data and proximity detectors (e.g., NFC sensors), it is also applicable to other types of sensor data and other types of sensors that can be used to provide additional indicators of the collective activity and/or its characteristics.

In some embodiments, the activities and characteristics of activities determined using methods 500, 600 and/or 700 may be sent to various computing devices. For example, activities such as rushing with the ball, passing the ball, tackling a ball carrier and their characteristics such as yards per rush, yards per pass, complete/incomplete pass, whether a tackle was a sack, etc. may be sent to a computing device configured to record statistics. In that sense, the techniques disclosed herein may provide for automated statistic tracking that can be provided to fans, coaches, broadcast staff, or the like. In another example, activities such as formation of the offense or defense and/or particular plays being executed may be sent to computing device configured to record such data for coaches, players, fans, etc. In a third example, activities and/or their characteristics may be provided to computing devices configured to produce a broadcast (e.g., via television, Internet, etc.). For example, visual displays of a player's speed, hit power, travel paths, or the like may be presented via graphical displays that may enhance viewer enjoyment of a game.

CONCLUSION

Many modifications and other embodiments will come to mind to one skilled in the art to which these embodiments pertain having the benefit of the teachings presented in the foregoing descriptions and the associated drawings. For example, the techniques discussed herein in the football context are applicable for activity determination in other contexts (e.g., sporting or otherwise). Furthermore, while tags and sensors are shown as being located on a human frame, the techniques discussed herein are also applicable to other objects, such as an animal or object frame. Therefore, it is to be understood that embodiments and implementations are not to be limited to the specific example embodiments disclosed and that modifications and other embodiments are intended to be included within the scope of the appended claims. Although specific terms are employed herein, they are used in a generic and descriptive sense only and not for purposes of limitation.

That which is claimed:

1. Apparel structured for wearing by an individual, the apparel comprising:
   a RF location tag supported by a first portion of the apparel associated with a first body position desirable for body motion kinetics information, the RF location tag configured to transmit blink data to at least one receiver, the blink data including first tag placement data indicative of placement of the RF location tag at the first body position, wherein the at least one receiver is configured to locate the RF location tag in a monitored area based on the blink data; and
   a proximity sensor supported by a second portion of the apparel associated with a second body position desirable for proximity information indicative of proximity to an object, the proximity sensor to transmit proximity data including a second indication of the second body position.

2. The apparel of claim 1, wherein:
   the first portion of the apparel corresponds to a first body joint;

the second portion of the apparel corresponds to a hand; and the object is a ball associated with a game involving the ball being carried by the hand.

3. The apparel of claim 1, wherein:

the first portion of the apparel corresponds to a shoulder;

the second portion of the apparel corresponds to a appendage; and the object is a ball with which the appendage interacts during a game.

4. The apparel of claim 1, wherein:

the apparel is a uniform;

the first portion of the apparel is a helmet; and the second portion of the apparel is a glove.

5. The apparel of claim 1, wherein:

the apparel is a uniform;

the first portion of the apparel is a helmet; and the second portion of the apparel comprises a sleeve.

6. The apparel of claim 1, wherein:

the apparel is a uniform;

the first portion of the apparel is a helmet; and the second portion of the apparel is an appendage article.

7. The apparel of claim 1, further comprising a power supply disposed in electrical communication with the RF location tag and the proximity sensor by a wired connection, which is at least partially sewn into the apparel.

8. The apparel of claim 1, further comprising an electrically conductive fabric configured to dispose a power supply in electrical communication with the RF location tag and the proximity sensor.

9. The apparel of claim 1, wherein the RF location tag is configured to transmit the blink data to the at least one receiver over a UWB communications channel.

10. The apparel of claim 9, wherein the blink data comprises time of arrival timing pulses that are used by the at least one receiver to determine tag location data.

11. A system comprising:

a RF location tag structured for wearing by an individual, the RF location tag configured to transmit blink data to at least one receiver of a monitored area, the blink data including first tag placement data indicative of placement of the RF location tag at a first body position desirable for body motion kinetics information;

a first proximity sensor structured for wearing by the individual in an article of apparel such that the first proximity sensor is positioned on the individual at a second body position desirable for proximity information indicative of the first proximity sensor being near an object of interest, wherein the object of interest includes a second proximity sensor, the first proximity sensor configured to detect proximity to the object of interest via the second proximity sensor, the first proximity sensor configured to transmit proximity data including second tag placement data indicative of placement of the first proximity sensor at the second body position.

12. The system of claim 11, wherein the RF location tag, the first proximity sensor, and a power supply are supported by the article of apparel.

13. The system of claim 11, wherein the article of apparel comprises an electrically conductive fabric configured to dispose a power supply in electrical communication with at least one of the RF location tag and the first proximity sensor.

14. The system of claim 11, wherein at least one of the RF location tag or the first proximity sensor receive power from heat generated by the individual.

* * * * *